(12) United States Patent
Martinez-Lorenzo et al.

(10) Patent No.: US 10,477,785 B2
(45) Date of Patent: Nov. 19, 2019

(54) ULTRASONIC-BASED SYSTEM FOR DETECTION OF METALLIC SECURITY THREATS CONTAINERS ON CARGO

(71) Applicant: Northeastern University, Boston, MA (US)

(72) Inventors: Jose A. Martinez-Lorenzo, Wellesley, MA (US); Yuri Alvarez Lopez, Langreo (ES)

(73) Assignee: Northeastern University, Boston, MA (US)

( * ) Notice: Subject to any disclaimer, the term of this patent is extended or adjusted under 35 U.S.C. 154(b) by 144 days.

(21) Appl. No.: 15/509,480

(22) PCT Filed: Oct. 21, 2015

(86) PCT No.: PCT/US2015/056755
§ 371 (c)(1),
(2) Date: Mar. 7, 2017

(87) PCT Pub. No.: WO2016/065066
PCT Pub. Date: Apr. 28, 2016

(65) Prior Publication Data
US 2017/0299552 A1   Oct. 19, 2017

Related U.S. Application Data

(60) Provisional application No. 62/066,586, filed on Oct. 21, 2014.

(51) Int. Cl.
| | |
|---|---|
| *G01N 29/06* | (2006.01) |
| *G01N 29/27* | (2006.01) |
| *A01G 31/02* | (2006.01) |
| *A01G 9/24* | (2006.01) |

(Continued)

(52) U.S. Cl.
CPC ............. *A01G 31/02* (2013.01); *A01G 9/246* (2013.01); *A01G 9/247* (2013.01); *A01G 25/16* (2013.01);
(Continued)

(58) Field of Classification Search
CPC ........ A01G 31/02; A01G 25/16; A01G 9/246; A01G 9/247; A01G 2031/006;
(Continued)

(56) References Cited

U.S. PATENT DOCUMENTS

2004/0232054 A1   11/2004   Brown et al.
2007/0276619 A1   11/2007   Sugahara et al.
(Continued)

FOREIGN PATENT DOCUMENTS

| WO | WO 2014/081721 | 5/2014 | |
|---|---|---|---|
| WO | WO-2016065066 A1 * | 4/2016 | ......... G01N 29/0654 |
| WO | WO-2016065066 A9 * | 8/2016 | ......... G01N 29/0654 |

OTHER PUBLICATIONS

International Search Report of PCT/US2015/056755 dated Apr. 8, 2016 entitled "Ultrasonic-Based System for Detection of Metallic Security Threats Containers on Cargo".
(Continued)

*Primary Examiner* — Daniel Pihulic
(74) *Attorney, Agent, or Firm* — Hamilton, Brook, Smith & Reynolds, P.C.

(57) ABSTRACT

Proactively identifying and interdicting transport of commodities associated with illicit nuclear materials and nuclear weapons shielded by high Z-number materials, such as lead, can help ensure effective nuclear nonproliferation. In an embodiment, a method for imaging an object on a surface includes exciting a surface with ultrasonic excitation from an ultrasonic transmitter having an ultrasonic transducer in contact with the surface. The method further includes imag-
(Continued)

ing, at a processor, a two-dimensional representation of the object acoustically coupled to the surface based on the ultrasonic reflections received at an ultrasonic receiver via a receiving transducer in contact with the surface. This method can complement existing x-ray screening systems to increase the odds of detecting radiological materials.

18 Claims, 22 Drawing Sheets
(12 of 22 Drawing Sheet(s) Filed in Color)

(51) Int. Cl.
    *A01G 25/16*     (2006.01)
    *A01G 31/00*     (2018.01)
(52) U.S. Cl.
    CPC ......... *G01N 29/0654* (2013.01); *G01N 29/27* (2013.01); *A01G 2031/006* (2013.01); *G01N 2291/015* (2013.01); *G01N 2291/0427* (2013.01); *G01N 2291/106* (2013.01); *G01N 2291/2695* (2013.01); *G01N 2291/2698* (2013.01); *Y02A 40/268* (2018.01); *Y02A 40/272* (2018.01); *Y02P 60/216* (2015.11)
(58) Field of Classification Search
    CPC ............... G01N 29/0654; G01N 29/27; G01N 2291/2698; G01N 2291/2695; G01N 2291/106; G01N 2291/0427; G01N 2291/015; Y02A 40/268; Y02A 40/272; Y02P 60/216

See application file for complete search history.

(56) References Cited

U.S. PATENT DOCUMENTS

| | | | |
|---|---|---|---|
| 2012/0206585 A1* | 8/2012 | Schneider | G01N 29/06 348/77 |
| 2013/0035901 A1 | 2/2013 | Breed | |
| 2014/0312350 A1* | 10/2014 | Schneider | G01N 29/06 257/66 |
| 2015/0286341 A1* | 10/2015 | Khuri-Yakub | G06F 3/0436 345/177 |
| 2017/0299552 A1* | 10/2017 | Martinez-Lorenzo | A01G 25/16 |

OTHER PUBLICATIONS

International Preliminary Report on Patentability dated Apr. 25, 2017 entitled "Ultrasonic-Based System for Detection of Metallic Security Threats Containers on Cargo".

\* cited by examiner

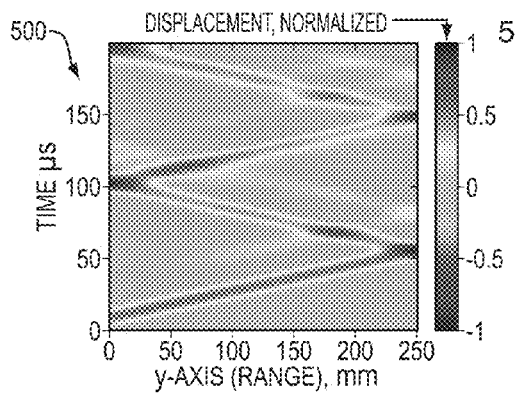
FIG. 5A1
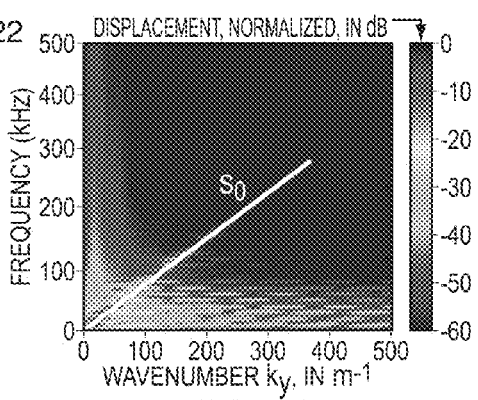
FIG. 5A2
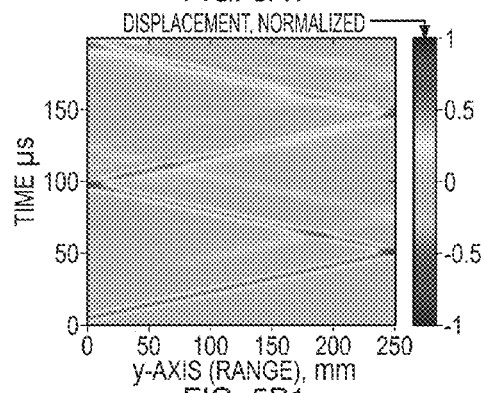
FIG. 5B1
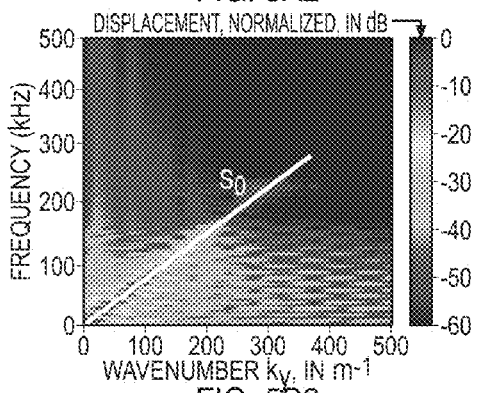
FIG. 5B2
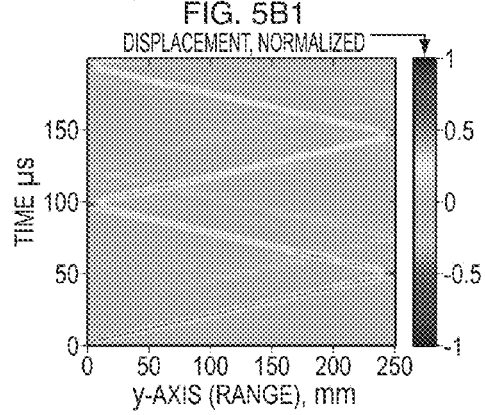
FIG. 5C1
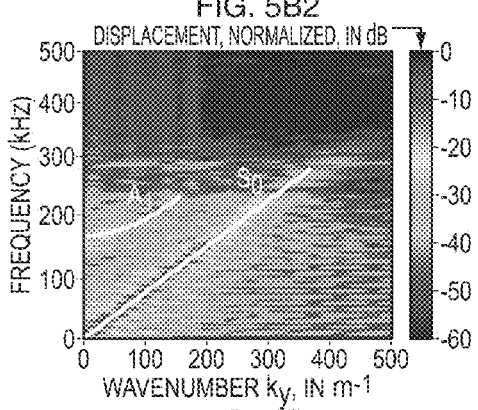
FIG. 5C2
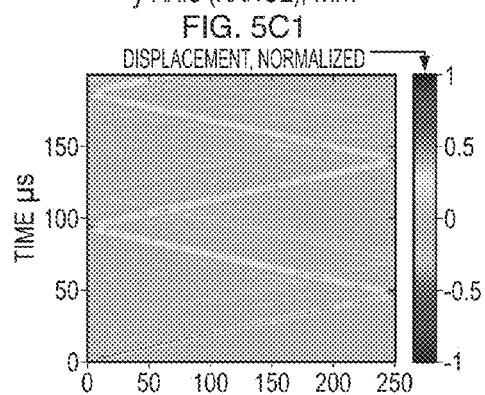
FIG. 5D1
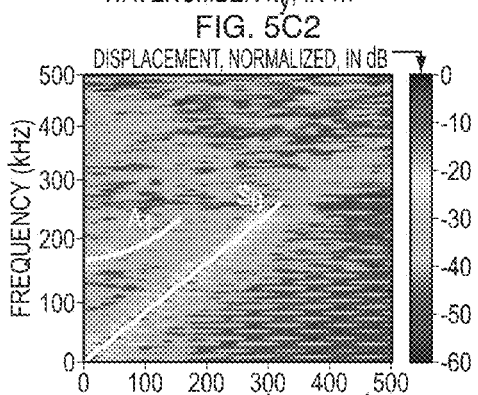
FIG. 5D2

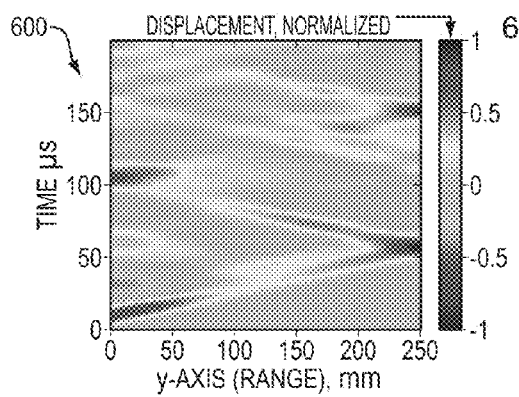
FIG. 6A1
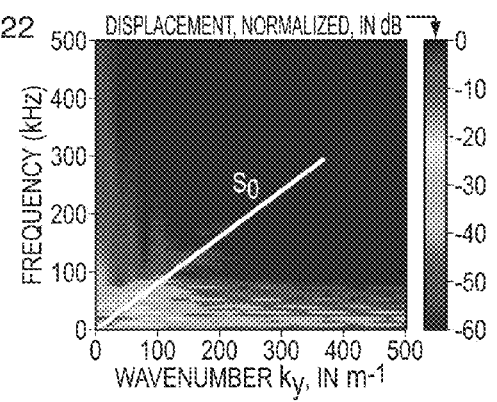
FIG. 6A2
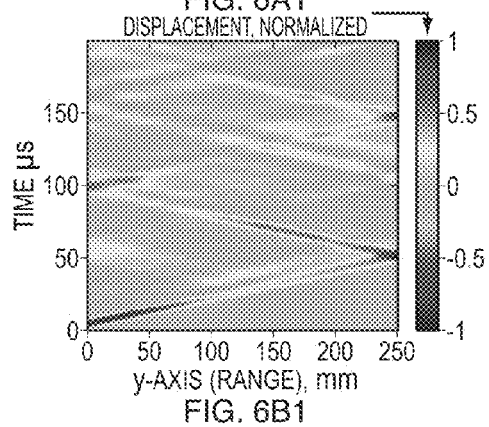
FIG. 6B1
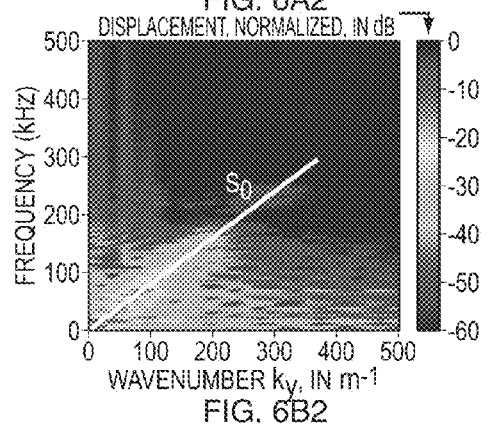
FIG. 6B2
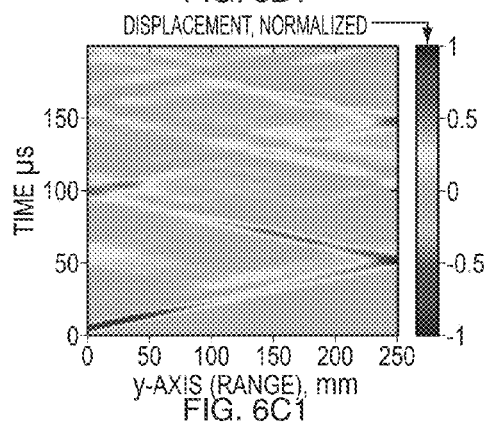
FIG. 6C1
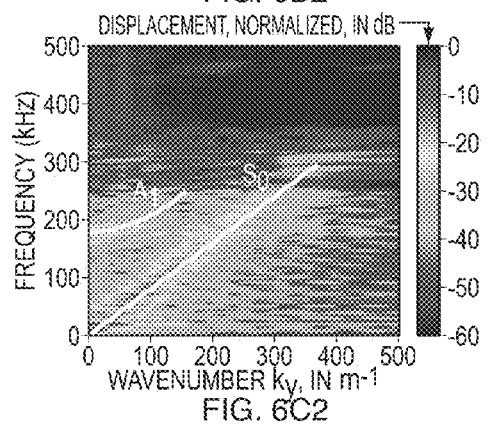
FIG. 6C2
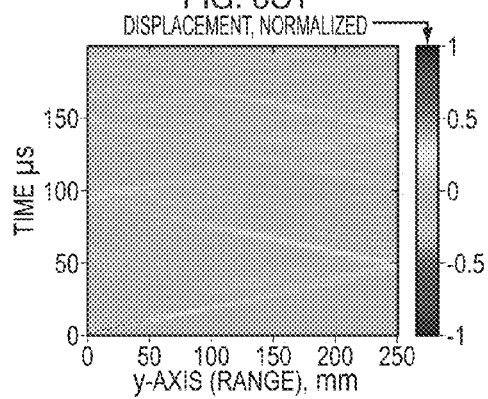
FIG. 6D1
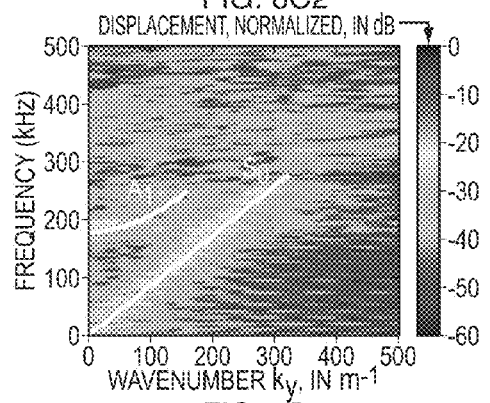
FIG. 6D2

1200

LAYOUT I: CONVENTIONAL FULL PHASED ARRAY

LAYOUT II: SPARSE TRANSMITTERS

LAYOUT III: SINGLE TRANSMITTER, FULL ARRAY OF RECEIVERS

ULTRASONIC-BASED SYSTEM FOR DETECTION OF METALLIC SECURITY THREATS CONTAINERS ON CARGO

RELATED APPLICATION

This application is the U.S. National Stage of International Application No. PCT/US2015/056755, filed Oct. 21, 2015, which designates the U.S., published in English, and claims the benefit of U.S. Provisional Application No. 62/066,586, filed Oct. 21, 2014. The entire teachings of the above applications are incorporated herein by reference.

GOVERNMENT SUPPORT

This invention was made with government support under Grant No. 2013-ST-061-ED0001 from the United States Department of Homeland Security. The government has certain rights in the invention.

BACKGROUND

Nonproliferation of nuclear threats is a critical objective in the war against nuclear terrorism. Proactively identifying and interdicting transport of commodities associated with illicit nuclear materials and nuclear weapons can help ensure effective nuclear nonproliferation.

Radioactive atoms are typically characterized for having a high atomic number Z (e.g., plutonium, having an atomic number Z of 94, and uranium, having an atomic number Z of 92). These radioactive atoms are unstable and give off various types of radiations, including gamma rays and neutrons. Gamma-ray spectrum analysis and neutron detectors, based on helium-3 gas, can be employed to detect nuclear radiological materials made out of radioactive atoms. Unfortunately, the signatures of these radiological materials can be diminished by enclosing them in a container made of other non-radiological, high Z number materials, such as lead (having an atomic number Z of 82). Such a container can hinder detection of the radiological materials by masking the signatures of radioactive atoms that are held within the container.

SUMMARY

Dual-energy radiography systems and X-ray back scattering can be successfully employed to detect the shielding materials, and are widely used in existing state-of-the-art cargo-inspection security portals. However, these types of detection can be difficult in cargo environments cluttered by high density materials.

Ultrasonic testing is used in a wide range of applications, such as structural health-monitoring, aircraft inspection, and medical imaging. Among existing ultrasonic techniques, employing guided waves (e.g., Lamb waves) is employed in applications such as rail and pipe testing, weld inspection, or aircraft lap joints. Guided wave imaging techniques have been developed for these purposes. A person of ordinary skill in the art can recognize that Lamb waves are waves that propagate in solid plates.

The imaging problem in guided wave structures becomes more challenging as the waveguide is bounded by reflecting interfaces. Optimal imaging needs to account for all ultrasonic reflections of the wave from each possible scatterer. To overcome this limitation, a matched filter-based imaging method can be employed to generate high resolution images, however, the match filter requires knowledge of the medium geometry.

Wave analysis in the wavenumber or Fourier domain has been also explored by existing techniques. For example, knowledge of the different modes propagating through the guided media can be used to recover information about the location of cracks and media inhomogeneities.

Reflected waves in the guided domain bounds may limit the performance of imaging methods for guided media. Embodiments of the present system and method perform real-time Fourier domain analysis after filtering-out plane wave components, thus removing non-desired contributions from the geometry bounds.

In an embodiment of the present invention, a novel sensing system and method, based on ultrasonic techniques, can detect 2D footprints of metallic materials traditionally used to conceal the radiological observation of nuclear threats. Use of the sensing system can improve the probability of threat detection of X-ray-based radiographic systems. An embodiment of the present invention is a fast, low-cost ultrasound imaging system, operating at 100 kHz, for example, capable of detecting metallic containers (e.g., those made of high Z number) inside trucks and/or containers. The system and method complements existing cargo screening systems (e.g., X-ray-based radiographic systems), thus enhancing the probability of detecting nuclear threats providing an additional, low-cost system by working in tandem with existing systems.

An array of ultrasonic transceivers having an ultrasonic transmitter and ultrasonic receiver can be coupled to a metallic structure (e.g., a surface or a floor), or "guided medium," of the truck to emit a guided, low-dispersive, Lamb wave. The guided medium creates reflections when the thickness or composition of the guided media is changed, and it can reveal the location of those changes and its associated reflections via image processing. Variation in the media composition and/or thickness of the metallic structure creates reflections that can be detected in images provided by image processing.

The knowledge of the reflection position provides information about the shielding containers location inside the truck. Moreover, due to the low coupling between the metallic surface of the truck and non-metallic surfaces that may be within the truck, only the footprint of metallic containers shows up in the imaging results, thus avoiding false positives from plastic or wooden assets. Plastic or wooden containers are not effective at shielding radiological material because they do not have a high atomic number, and therefore do not need to be detected. As imaging capabilities are degraded if working with dispersive Lamb wave modes, the operating frequency is tuned to provide a trade-off between low dispersion and real-time image resolution.

In an embodiment, a method for imaging an object on a surface includes exciting a surface with ultrasonic excitation from an ultrasonic transmitter having a transmitting ultrasonic transducer in contact with the surface. The method further includes imaging, at a processor, a two-dimensional representation of the object acoustically coupled to the surface based on the ultrasonic reflections received at an ultrasonic receiver via a receiving ultrasonic transducer in contact with the surface.

In an embodiment, the method can further include moving (1) the surface relative to the ultrasonic transmitter and ultrasonic receiver or (2) the ultrasonic transmitter and ultrasonic receiver relative to the surface; or (3) not moving either of them and just having an ultrasonic array that spans the whole length of the plate. In some embodiments, the ultrasonic transmitter and ultrasonic receiver have respective transducers co-located with the respective electronics used to perform the transmitting and receiving functions, respectively.

In an embodiment, the ultrasonic transmitter is an array of ultrasonic transmitters spanning a substantial length of the surface, and the ultrasonic receiver is an array of ultrasonic receivers spanning the substantial length of the surface.

In an embodiment, the method further includes filtering, at the processor, plane waves from the ultrasonic reflections based on (i) time elapsed since exciting the surface and (ii) the size of the surface. The filtering reduces effects of multipath reflections.

In an embodiment, the surface is an internal surface of a container.

In an embodiment, the method can excite the surface with ultrasonic excitation by exciting the surface sequentially with a range of frequencies. The range of frequencies can be based on a thickness of the surface and a material of the surface. The surface can further be associated with an identifier. The method can further, based on the identifier, load representations of a thickness of the surface and a material of the surface from data storage. The method can further automatically determine the range of frequencies to use based on the representations of the loaded thickness and loaded material.

In an embodiment, the imaging includes calculating displacement of a wave resulting from the transmitted ultrasonic excitation in the frequency domain by performing a Fourier transform of an observation of the ultrasonic reflections of the ultrasonic excitation in the time domain.

In an embodiment, the ultrasonic reflections are received at multiple ultrasonic receivers. The number of multiple ultrasonic receivers corresponds with the number of ultrasonic transmitters in some embodiments.

In an embodiment, the method includes exciting the surface by emitting ultrasonic excitations orthogonal, parallel, or orthogonal and parallel to the surface at a point of contact of the transducer of the ultrasonic transmitter.

In an embodiment, a system for imaging objects on a surface includes an ultrasonic transmitter having an ultrasonic transducer in contact with a surface configured to excite the surface with ultrasonic excitation. The system further includes an ultrasonic receiver in contact with the surface configured to receive ultrasonic reflections of the ultrasonic excitation. The system further includes a processor and a memory with computer code instructions stored therein. The memory is operatively coupled to the processor such that the computer code instructions configure the processor to implement an imaging module configured to image a two-dimensional representation of the object acoustically coupled to the surface based on the received ultrasonic reflections.

In an embodiment, the system also includes a motion module configured to move (1) the surface such that the surface moves relative to the ultrasonic transmitter and ultrasonic receiver, (2) the ultrasonic transmitter and ultrasonic receiver such that the ultrasonic transmitter and ultrasonic receiver move relative to the surface, (3) both the surface and the ultrasonic transmitter and receivers moving, or (4) an array that covers the whole length of the surface's side.

In another embodiment, the ultrasonic transmitter can be an array of ultrasonic transmitters spanning a substantial length of the surface. The ultrasonic receiver can be an array of ultrasonic receivers spanning the substantial length of the surface.

In an embodiment, the processor can be further configured to filter plane waves from the ultrasonic reflections based on (i) time elapsed since exciting the surface and (ii) the size of the surface. The filtering reduces the effects of multipath reflections.

In an embodiment, the surface is an internal surface of a container.

In an embodiment, the ultrasonic transmitter is further configured to excite the surface with ultrasonic excitation by exciting the surface sequentially with a range of frequencies. The range of frequencies may be based on a thickness of the surface and a material of the surface.

In an embodiment, the surface can be associated with an identifier. The processor can be further configured to, based on the identifier, load representations of a thickness of the surface and a material of the surface. The processor can be further configured to determine the range of frequencies to be used by the imaging algorithm automatically based on the loaded representations of the thickness and loaded material.

In an embodiment, the processor can be further configured to image by calculating displacement of the wave resulting from the transmitted ultrasonic excitation in the frequency domain by performing a Fourier transform of an observation of the ultrasonic reflections of the ultrasonic excitation in the time domain.

In an embodiment, the ultrasonic receiver can include a plurality of ultrasonic receivers corresponding with the number of ultrasonic transmitters.

In an embodiment, the ultrasonic transmitter can be further configured to excite the surface by emitting ultrasonic excitations that are orthogonal, parallel, or orthogonal and parallel, to the surface at a point of contact of the transducer of the ultrasonic transmitter.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 5A-D(1-2) are screen prints of captured data of recorded time-cross-range displacement along x=40 cm and x=22 cm lines.

FIG. 6A-D(1-2) are screen prints of captured data of transformed response in the frequency-wavenumber domain corresponding to FIGS. 5A-D(1-2).

DETAILED DESCRIPTION

A description of example embodiments of the invention follows.

Figure 1:
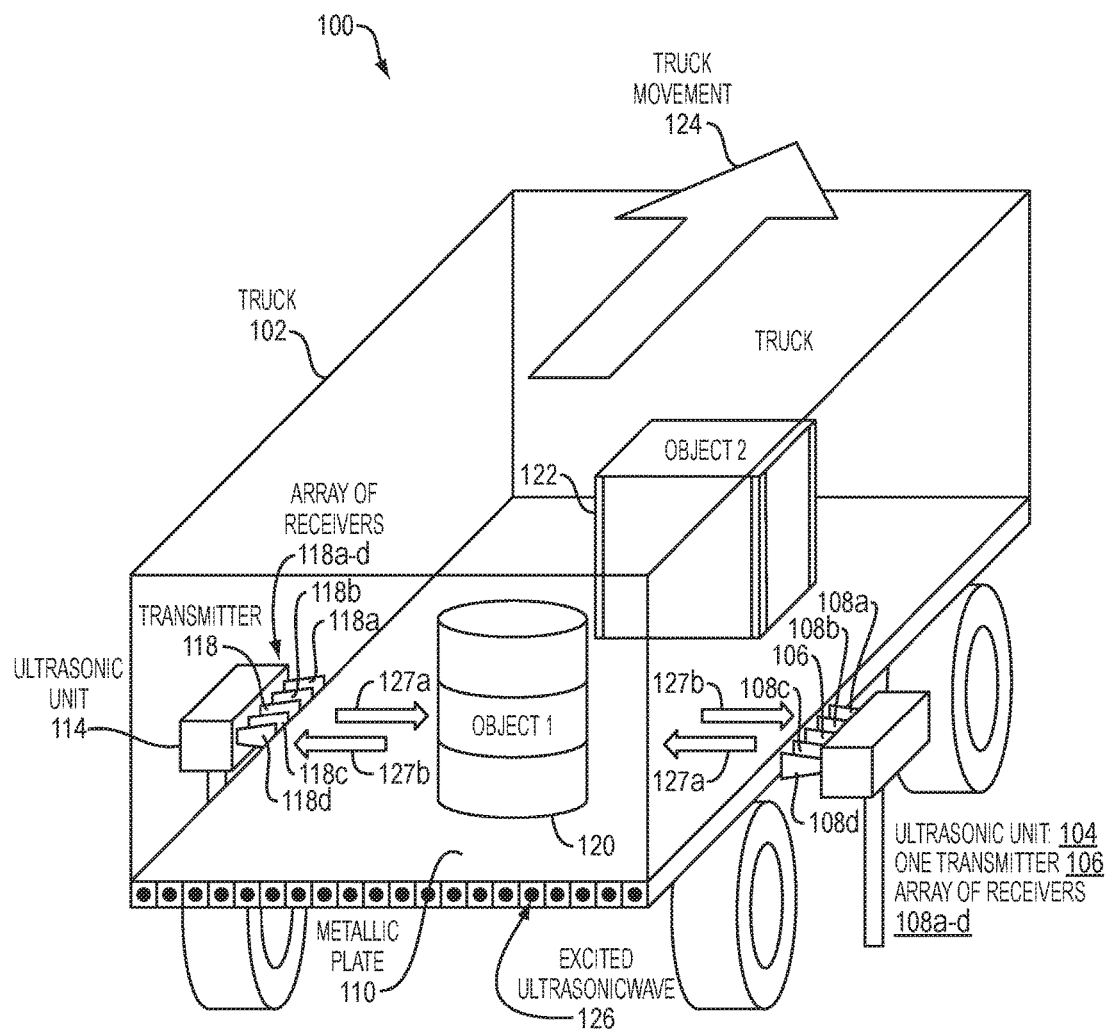
FIG. 1 is a diagram illustrating an example embodiment of the present invention.

FIG. 1 is a diagram 100 illustrating an example embodiment of the present invention. A truck 102 having a metallic plate 110 as a surface has located thereon two objects, Object 1 120 and Object 2 122. The truck 102, in many circumstances, needs to have its contents checked by Customs of a country or other security. As described above, dual-energy radiography systems and X-ray back scattering are examples of systems to check contents of a truck 102 for hazardous material, such as radiological material. While dual-energy radiography systems and X-ray back scattering can detect radiological materials, they can miss such detection if the radiological materials are housed in a material with a high atomic number, such as lead. These surfaces are heavy, and likely placed on the floor, in most cases a metallic plate 110 of the truck 102. Further, surfaces with such a heavy atomic number are likely to acoustically couple with the metallic plate 110. In an embodiment of the present invention, ultrasonic units 104 and 114 can be employed to provide a complementary security system that increases the chances of discovering containers able to shield hazardous material by sending and receiving ultrasonic waves, and imaging objects 120 and 122 on the metallic plate 110. Where X-ray back scattering systems can detect unshielded radiological materials, the present system can detect containers that shield such radiological materials. In tandem, both systems can detect the unshielded materials and many containers that shield the signature of radiological materials, therefore increasing the chances of detection of radiological materials overall.

The ultrasonic units 104 and 114 include a respective transmitter 106 and 118, and a respective array of receivers 108a-d and 118a-d. In other embodiments, the ultrasonic units 104 and 114 can have one transmitter 106 and 118 for each receiver, or can be an array of multiple transmitters and multiple corresponding receivers. The respective transmitters 104 and 114 and respective arrays of receivers 108a-d and 118a-d are coupled to the metallic surface 110 of the truck 102 to emit ultrasonic waves and receive corresponding reflections thereof.

The truck 102 moves 124 relative to the ultrasonic units 104 and 114 so that the excited ultrasonic waves 126 can be emitted across the length of the metallic plate 110, where the transmit directions are indicated by arrows 127a and the receive directions are indicated by arrows 127b. Each excited ultrasonic wave 126 images the metallic plate 110 in a line, or rectangular area, orthogonal to the ultrasonic units' 104 and 114 coupling to the metallic surface. Moving the truck 102 relative to the ultrasonic units 104 and 114 images the metallic surface in subsequent adjacent lines/rectangular areas until the metallic plate 110 of the truck has been imaged. The truck 102 can be moved relative to the ultrasonic units 104 and 114 by either the truck's 102 moving and the ultrasonic units' 104 and 114 being stationary, the ultrasonic units 104 and 114 moving and the truck 102 remaining stationary, or both the truck 102 and ultrasonic units 104 and 114 moving. Alternatively, an array of ultrasonic units 104 and 114 can be placed along the truck to emit excitation ultrasonic waves 126 along the metallic plate 110, such that relative motion of the truck 102 to the ultrasonic units 104 and 114 is not required. Regardless of the setup of the ultrasonic units 104 and 114 and movement relative to the truck, from the reflections, a two-dimensional (2D) image of objects on the metallic plate 110 can be imaged according to the systems and methods described herein.

Figure 2:
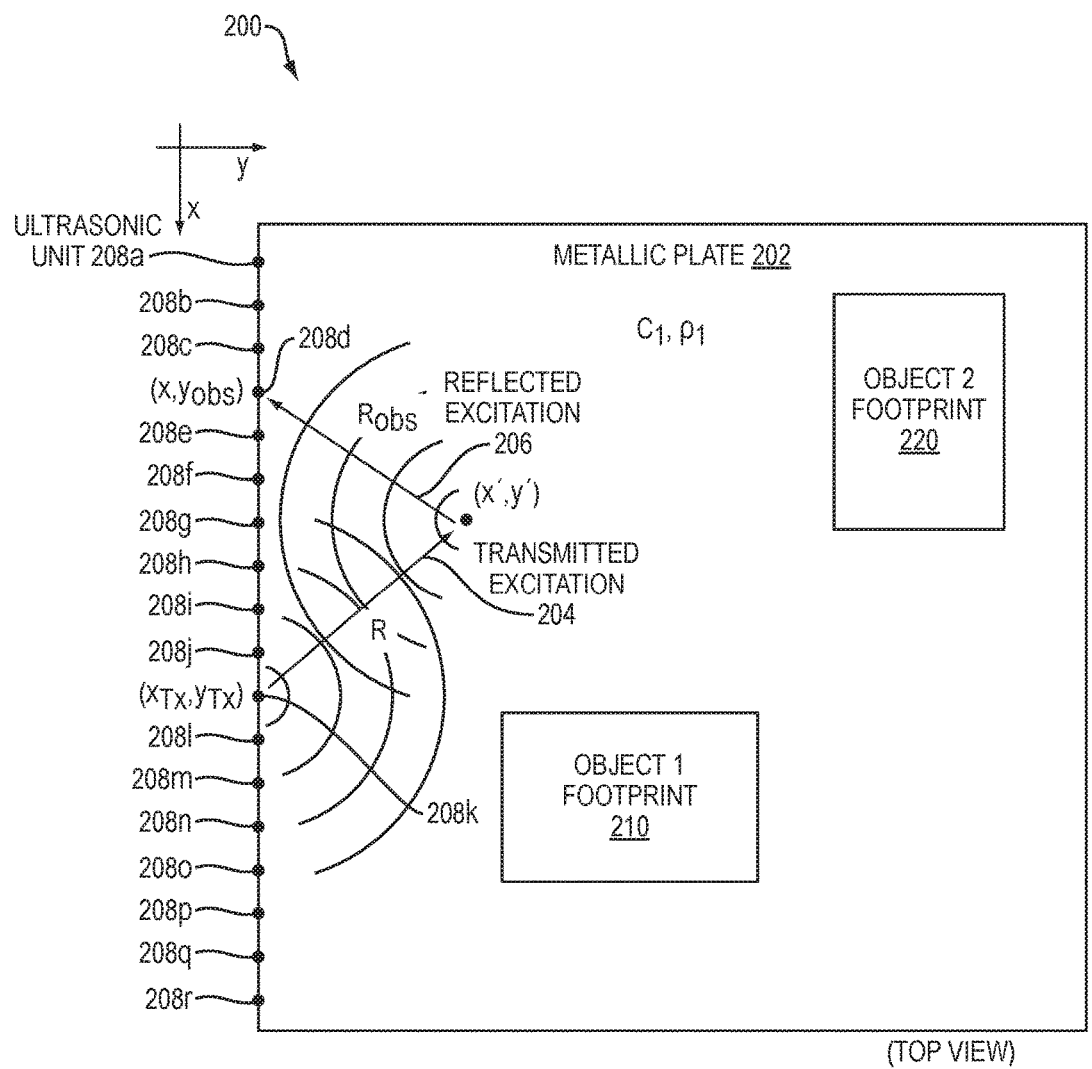
FIG. 2 is a schematic diagram of a top view illustrating an example embodiment of an alternative configuration of the ultrasonic imaging system of FIG. 1.

FIG. 2 is a schematic diagram 200 of a top view illustrating an example embodiment of an ultrasonic imaging system configured to image a metallic plate 202 (e.g., surface or medium). Ultrasonic units 208a-r are distributed along the x-axis of the metallic plate 202, and therefore have a fixed y-position, $y_{obs}$, because they are fixed on a common axis. As described above, each ultrasonic unit 208a-r includes at least one ultrasonic transmitter and ultrasonic receiver. Range is y-axis (depth), and cross-range is x-axis (aperture). An ultrasonic transmitter of the ultrasonic unit 208k transmits a transmitted excitation 204 on the metallic plate 202, and a reflected excitation 206 ($R_{Obs}$) is received at an ultrasonic receiver of the ultrasonic unit 208d, among others.

Imaging domain points are denoted as (x', y'). Imaging domain ultrasonic reflectivity, denoted by the function ρ(x', y'), can be estimated from the displacement in the frequency domain recorded in the receivers, $U(x, y_{obs}, f)$ over a certain frequency bandwidth, B (spanning from 0 to $f_{max}$), by backpropagating the recorded displacement, adding them coherently. For the case of a single evaluation point (x', y'), reflectivity is given by Equation 1, below:

$$\rho(x'',y')=\Sigma_x\Sigma_f U(x,y_{obs},f)\exp(jk_1R_{obs})\exp(jk_1R), f=[0:\Delta f:f_{max}] \quad (1)$$

where $k_1$ is the medium wavenumber, $k_1=2\pi f/c_1$, and $c_1$ is the Lamb mode excitation velocity in the supporting medium (e.g., the metallic structure of the truck).

R and $R_{obs}$ are defined in Equations 2 and 3, below:

$$R=((x_{Tx}-x')^2+(y_{Tx}-y')^2)^{1/2} \quad (2)$$

$$R_{obs}=((x-x')^2+(y_{obs}-y')^2)^{1/2} \quad (3)$$

with ($x_{Tx}$, $y_{Tx}$) being the position of the ultrasonic transmitter. $\Delta f$ is the frequency sampling rate. If the displacement is recorded in a time interval t at every receiving position x, $u(x, y_{obs}, t)$ ranging from $t_1$ to $t_2$, in $\Delta t$ time steps, then, the relationship between time and frequency is as shown in Equations 4 and 5 below:

$$f_{max}=1/\Delta t \quad (4)$$

$$\Delta f=1/(t_2-t_1) \quad (5)$$

The displacement in the frequency domain, $U(x, y_{obs}, f)$, is calculated by simply taking the Fourier transform of the recorded displacement in the time domain, $u(x, y_{obs}, t)$, as shown in Equation 6 below:

$$U(x,y_{obs},f)=\Sigma_t u(x,y_{obs},t)\exp(-j2\pi ft), t=[t_1:\Delta t:t_2] \quad (6)$$

The imaging system is proposed to be used in a guided medium, such as a metallic plate which thickness much smaller than its width and length. Reflections in waveguide sides create non-desired responses in the resulting image that degrade the system performance. To overcome this limitation, the observed displacement can be analyzed in the Fourier domain, filtering out non-desired plane wave contributions. As $y_{obs}$ is constant (e.g., the position of the aperture in the range axis), only the Fourier transform across x-axis (e.g., cross-range) needs to be calculated:

$$U_k(y_{obs},k_x,f)=\int_x U(x,y_{obs},f)\exp(-jk_x x)dx \quad (7)$$

$k_x$ is the x-component of the $k_1$ wavenumber, ranging from $-\pi/\Delta x$ to $\pi/\Delta x$, where $\Delta x=x_2-x_1$, is the sampling rate of the aperture (cross-range axis) [23]. The spectral resolution, $\Delta k_x$, is inversely proportional to the aperture size, $L_{Rx}$:

$$\Delta k_x=2\pi/L_{Rx} \quad (8)$$

By expressing the observed displacement in the Fourier domain, different plane wave contributions, or in other words, different angle-of-arrival, can be identified. For this purpose, frequency axis is mapped into $k_y$ axis:

$$k_y=(k_1^2-k_x^2)^{1/2} \quad (9A)$$

Figure 3:
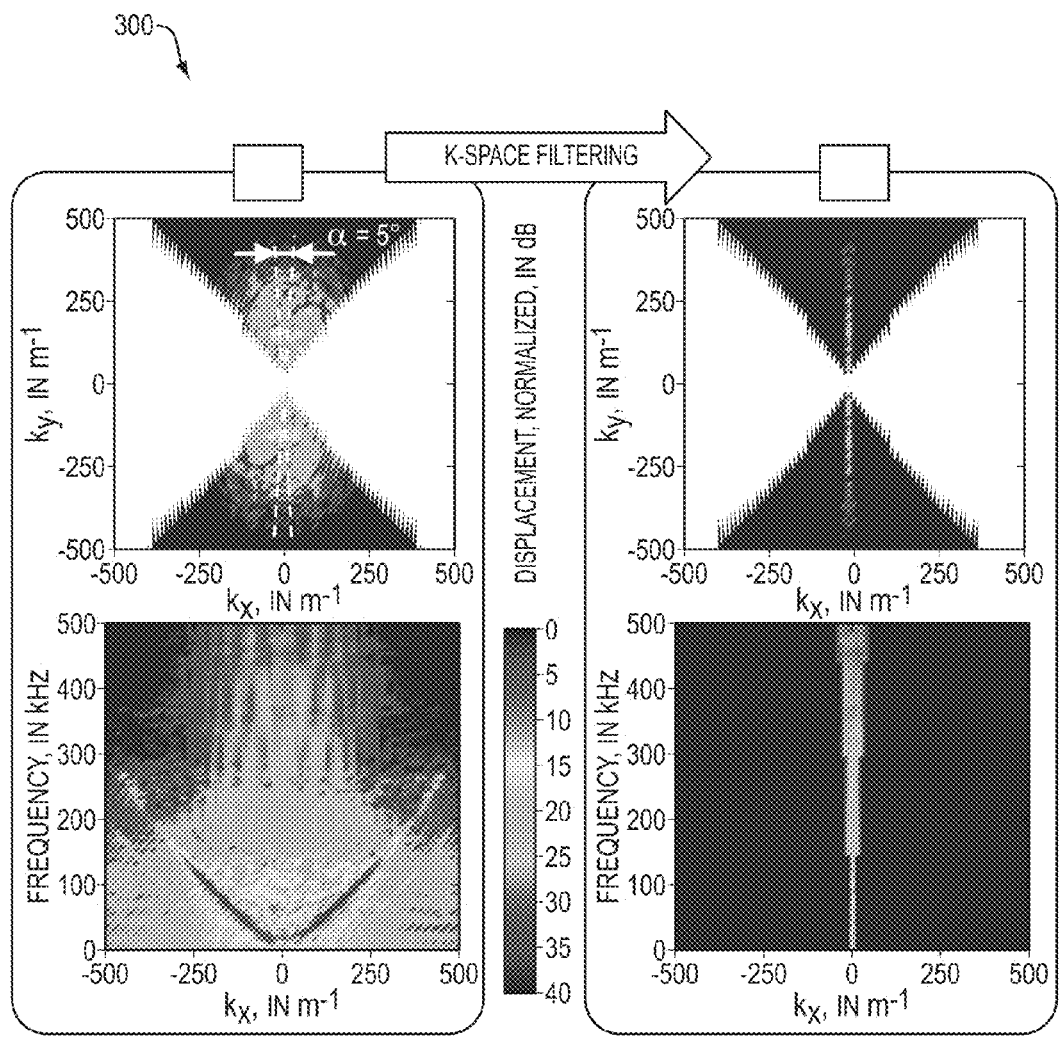
FIG. 3 is a diagram illustrating a plane wave spectrum of an observed displacement represented in the $k_x$, $k_y$-domain, which identifies an angle-of-arrival of different plane wave components.

FIG. 3 is a diagram 300 illustrating a plane wave spectrum of the observed displacement represented in the $k_x$, $k_y$-domain, which identifies the angle-of-arrival of the different plane wave components.

Reflections in waveguide limits can be identified with those plane wave components with large angle-of-arrival values. In a limit case, filtering out all the plane wave components with angle-of-arrival greater than 0° would allow to identify the range position of all the objects within the waveguide, but at the expense of losing cross-range information. Thus, a trade-off between range and cross-range information retrieval is set, by filtering out all the plane wave components with angle-of-arrival larger than α:

$$U_{k,filtered}(y_{obs},k_y,k_x)=\{U_k(y_{obs},k_y,k_x) \text{ if } a \tan(k_y,k_x)<\alpha; 0 \text{ otherwise}\} \quad (9B)$$

Finally, the filtered displacement in the Fourier domain is transformed back into the spatial x, y-domain:

$$U_{filtered}(x,y_{obs},f)=\int_y U_{k,filtered}(y_{obs},k_y,k_x)\exp(+jk_x x)dx \quad (10)$$

Ultrasonic reflectivity can be recovered by applying Eq. 1. In this case, responses due to reflections in walls with angles larger than α do not appear in the recovered ultrasonic reflectivity image.

Figure 4:
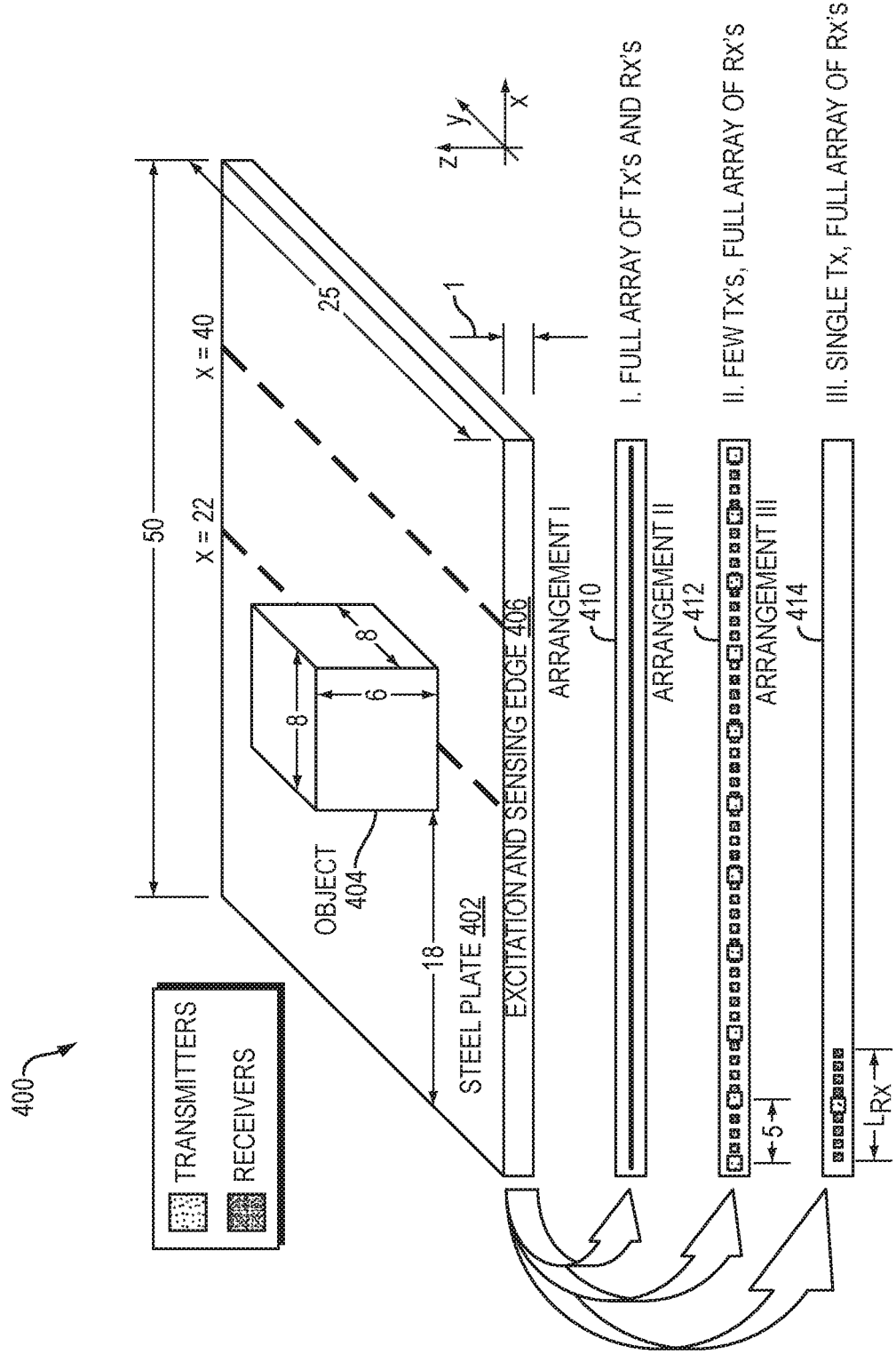
FIG. 4 is a diagram illustrating an example of a single 1 cm thick metallic steel plate having an object on it and alternative embodiments of transmitters and receivers coupled thereto.
Figure 15:
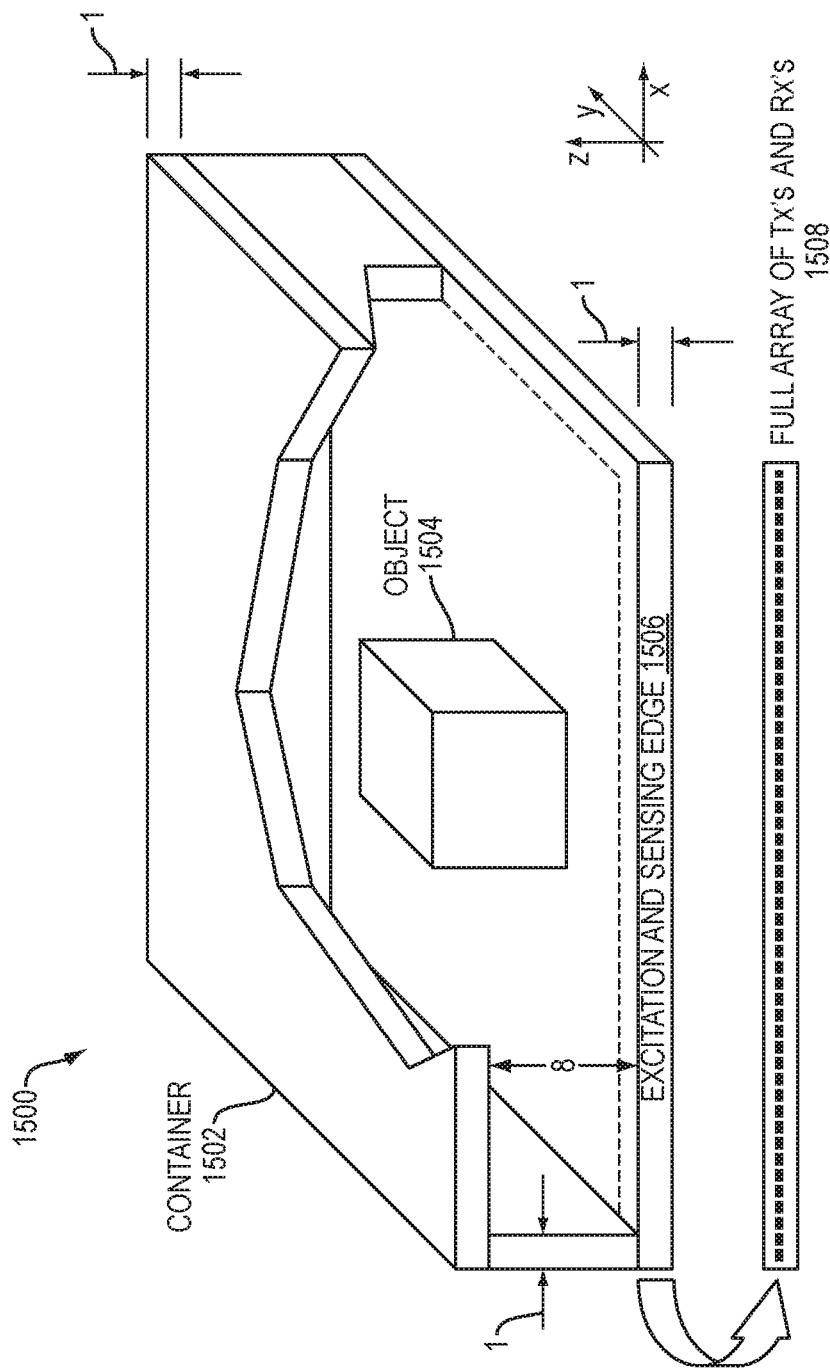
FIG. 15 is a diagram illustrating a container storing an object therein and an excitation and sensing edge at a forefront of the container with respect to a viewing perspective.
Figure 17:
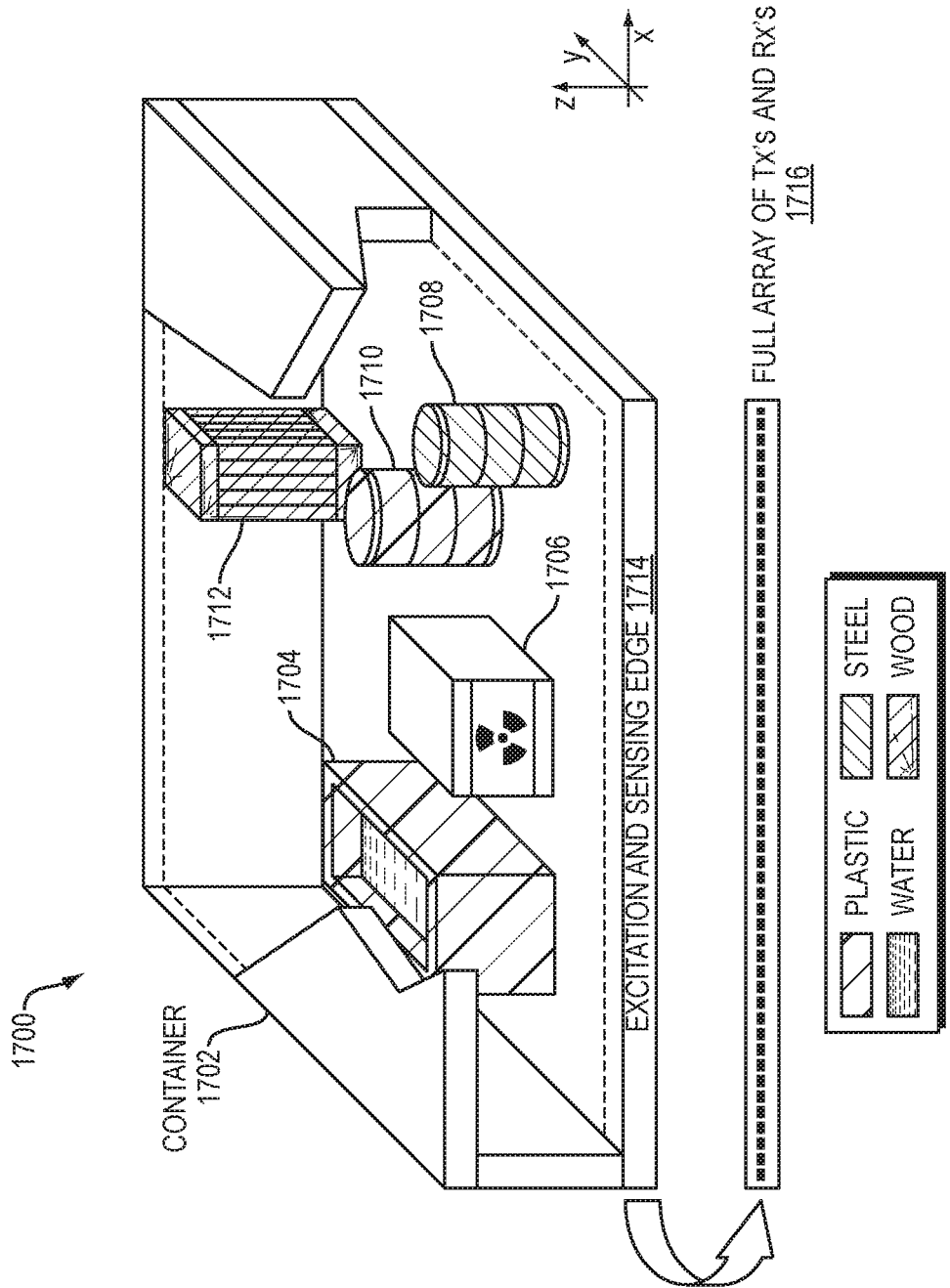
FIG. 17 is a diagram illustrating another example of a container having objects stored therein and an excitation and sensing edge.

Three simulation-based examples are shown in FIG. 4, FIG. 15, and FIG. 17, respectively, each having more complex and realistic scenario than its predecessor. The forward ultrasonic problem is simulated using a 3D finite-element method (FEM).

Thicknesses of the metallic and non-metallic plates are the same as in a full-size problem, so the proposed modal analysis and imaging methodology can be straightforwardly employed in simulated or measured data from large scattering problems. Additionally, the proposed un-optimized imaging processing can be employed in real-time time applications because it is currently executed in less than 5 s in the aforementioned conventional laptop.

FIG. 4 is a diagram 400 illustrating a first example having a single 1 cm thick metallic steel plate 402 with an object 404 on it. The simulation parameters for steel are the following: P-wave velocity 5960 m/s, S-wave velocity 3220 m/s, and density 8000 kg/m3.

Three embodiments of excitation and recorded displacement layouts can be employed, as shown by Arrangements I, II, and III 410, 412, and 414, respectively. The Arrangement I 410 includes a full array of transmitters and receivers placed along the $y_{obs}=0$ m side of the plate. In this Arrangement I 410, separation between array elements is 1 cm, thus yielding 50 transmitters and 50 receivers. However, this cross-range (e.g., x-axis) sampling rate is taken to avoid spatial aliasing, which is proportional to the separation between array elements. A person of ordinary skill in the art can employ other separation of the array elements that also avoid spatial aliasing. In arrangement I 410, all the elements transmit at the same time, exciting a plane wave that propagates generally along the y-axis (e.g., range). This configuration is equivalent to a phased array system where all the elements transmit with the same delay.

After transmission, the ultrasonic waves/excitations (e.g., Lamb wave modes) are analyzed. Concerning the imaging application purpose, low-dispersive modes are required, thus setting a trade-off between the use of high frequencies where dispersive modes are created, and lower frequencies that provide poorer imaging resolution.

FIGS. 5A-D(1-2) are screen prints 500 of captured data of recorded time-cross-range displacement along x=40 cm and x=22 cm lines.

FIG. 6A-D(1-2) are screen prints 600 of captured data of transformed response in the frequency-wavenumber domain corresponding to FIGS. 5A-D(1-2).

Data processing for the ultrasonic waves/excitations (e.g., Lamb wave modes) calculation follows a two-dimensional (2D) Fourier Transform of the recorded displacement.

A windowed tone burst is chosen as the excitation signal. The length of the rectangular window is equal to one period of the tone. Center frequencies from 50 kHz to 400 kHz can be employed based on the material, material's thickness, and material's shape and dimensions. The excitation signal bandwidth is 100% with respect to the tone frequency (e.g. from 25 to 75 kHz for the 50 kHz windowed tone burst). These excitation signals are chosen as a tradeoff between dispersion and range resolution. Larger bandwidth improves range resolution, but at the expense of increasing dispersion. Time axis is sampled every $\Delta t=1$ us, recording the displacement from $t_1=0$ us to $t_2=200$ us.

Either when considering the x-cut without (x=40 cm, FIG. 5) or with the metallic box on top of the plate (x=22 cm, FIG. 6), only the $S_0$ mode is present up to 100 kHz. For higher excitation frequencies, $S_0$ and $A_1$ modes are excited. Thus, to avoid significant dispersion that degrades imaging results, a 100 kHz excitation tone is considered in further examples.

With respect to FIG. 5, once the frequency of the excitation tone is chosen, imaging results for transmitting and receiving configuration Arrangement I 410 are retrieved. In this case, the receivers record the displacement along y=0 m line.

Figure 7:
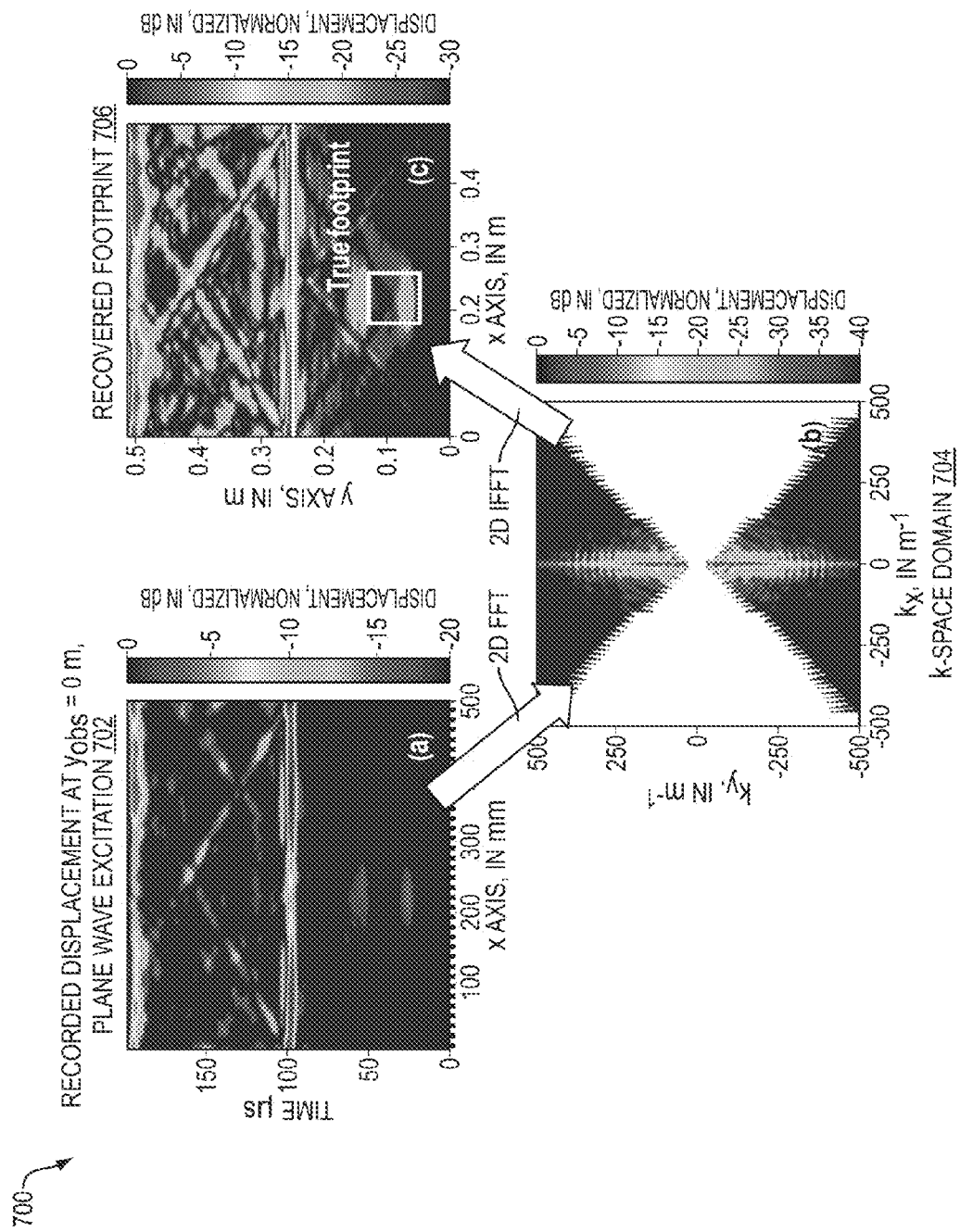
FIGS. 7A-C are screen prints of captured data of a plot of (A,C) time-cross range response, where the light blue reflections happening at the y=25 cm edge and the front and rear metallic plate-box interfaces are clearly visible, and (B) plane wave spectrum, respectively.
Figure 8A:
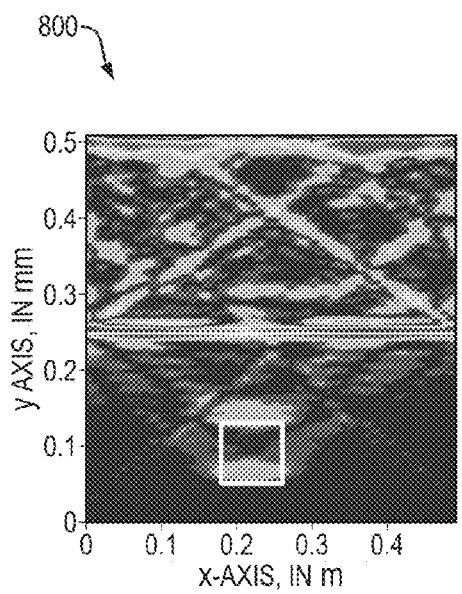
FIG. 8A-D are screen prints of captured data of recovered images for different Δx values ranging from 1 cm to 10 cm.
Figure 8B:
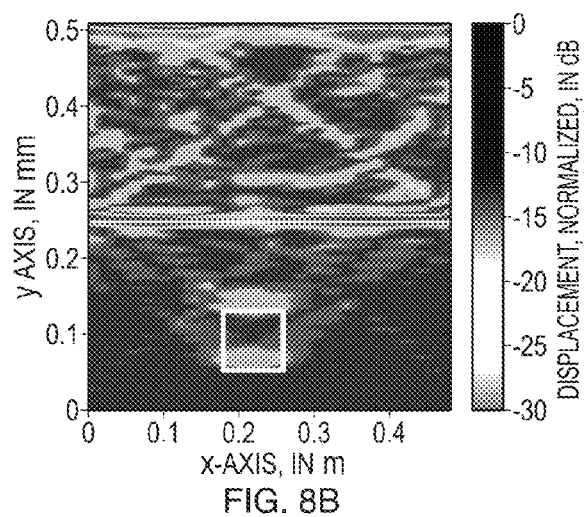
Figure 8C:
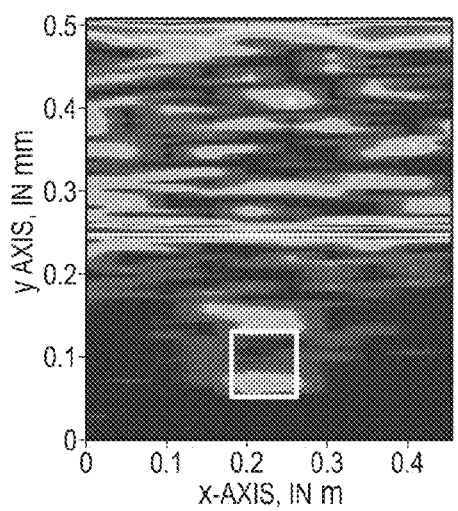
Figure 8D:
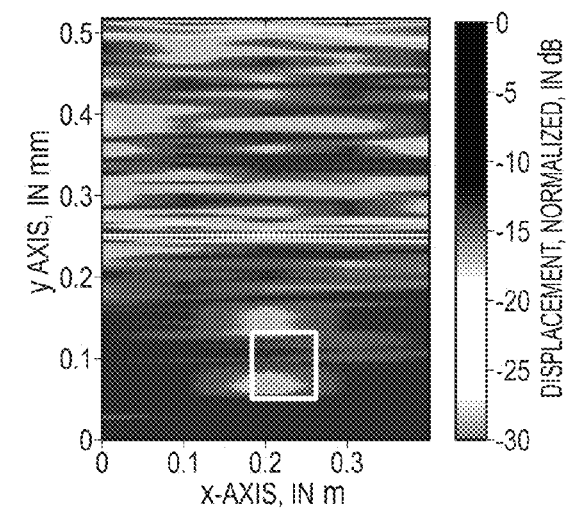

FIGS. 7A-C are screen prints 702, 704 and 706 of captured data. Screen print 702 illustrates an example of a plot of time-cross range response, where the light blue reflections happening at the y=25 cm edge and the front and rear metallic plate-box interfaces are clearly visible, which is also shown by the screen print 706 by the purple box. Note that also the second reflection is also noticeable in corresponding locations in both screen print 702 and 706. After the first reflection, edge plate modes distort the backpropagated displacement, which are seen as the X-shape features observed screen print 702.

The reflection at the edge of the plate (e.g., y=25 cm) opposed to the transmitter can be used together with the a-priori knowledge of the plate width to recover an accurate estimation of the Lamb mode excitation velocity, $c_1$. As the distance at which the opposite edge reflection happens is a known value (e.g., the plate width), a person of ordinary skill in the art can calculate the $c_1$ value to set this reflection in place (e.g., $c_1$=5100 m/s).

The recorded displacement is transformed into the k-space by taking the Fast Fourier Transform across time and cross-range (x–) axis (Eqs. 6 and 7). The plane wave spectrum is plotted in screen print 704. As the array of transmitters create a plane wavefront, most of the wavemodes correspond to normal direction of arrival. Finally, the wavemodes are transformed back in the range-cross-range imaging domain, yielding the footprint image depicted in FIG. 7C. The backpropagated displacement matches the true footprint of the considered layout.

As described above, separation between sensors in the cross-range, or x–, axis, $\Delta x$, are chosen to prevent aliasing.

FIG. 8A-D are screen prints 800 of captured data illustrating recovered images for different $\Delta x$ values ranging from 1 cm to 10 cm. As $\Delta x$ values increase, the cross-range image resolution decreases across screen prints 800.

Referring back to FIG. 4, for the considered arrangement of transmitters and receivers (Arrangement I 410), k-space domain filtering does not significantly impact the improvement of the image quality because most of the wavemodes are in the $k_x=0$ axis.

The effectiveness of k-space filtering is shown in Arrangement II 412, which includes a single transmitter and a full array of receivers. The number of receiving elements is again 50, with $\Delta x=1$ cm spacing. A point source-like transmitter is considered, creating a cylindrical pressure wave.

Figure 9:
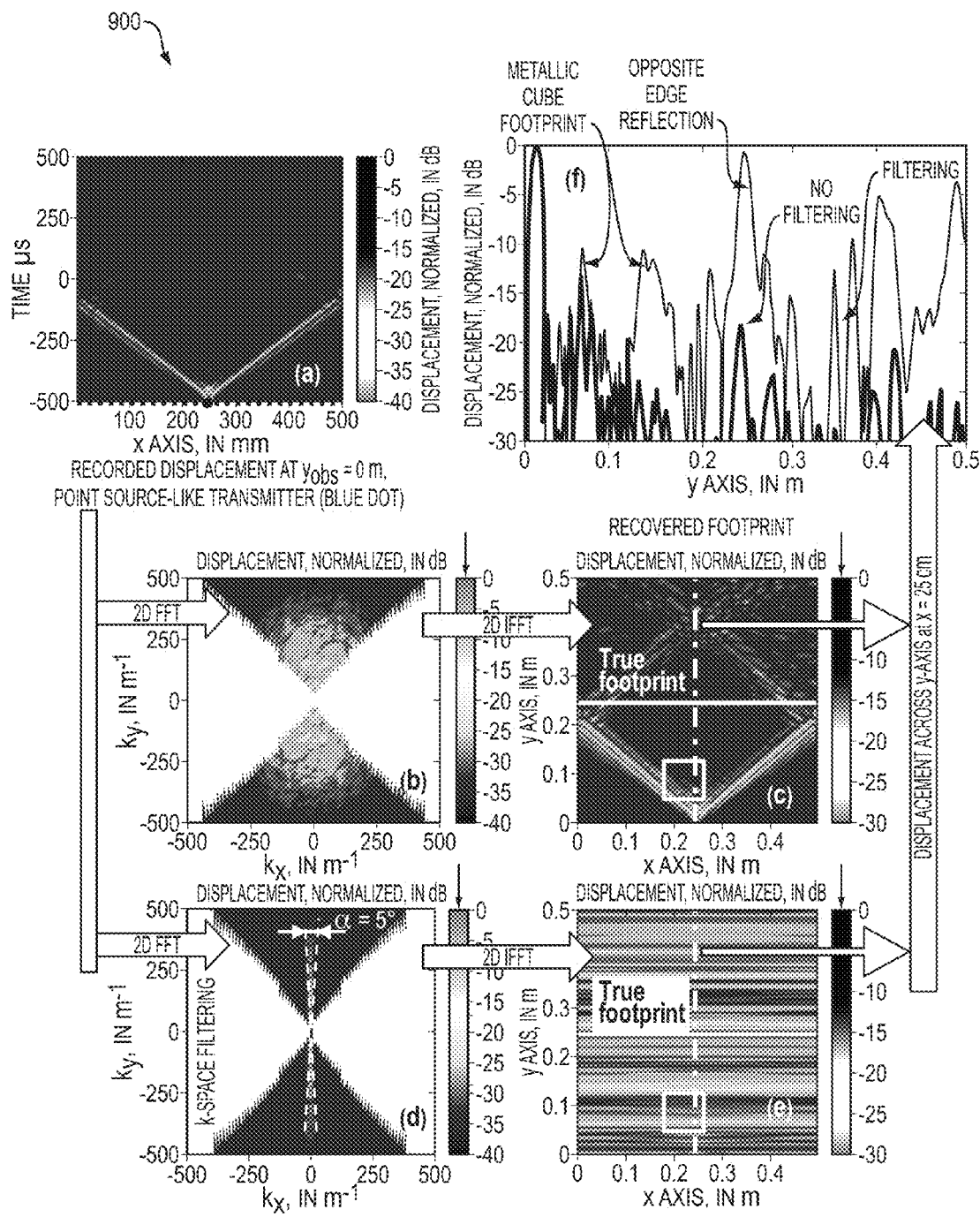
FIG. 9A is a screen print of captured data of the recorded time-cross-range displacement for a single transmitter placed at $x_{Tx}$=25 cm (with $x_{Tx}$ being the position of the transmitter).
FIG. 9B is a screen print of captured data of the k-space response showing plane wave components propagating in all the possible travelling directions (e.g., filling the k-space domain), as expected for a cylindrical wave.
FIG. 9C is a screen print of captured data illustrating backpropagated displacement on neither the footprint of the box nor the plate edge at y=25 cm, but the wavefront of the cylindrical wave.
FIG. 9D is a screen print of captured data illustrating a filtered k-space d-domain, where only components with kx<<ky remain.
FIG. 9E is a diagram illustrating backpropagated displacement of the filtered wavemodes, where the reflections happening at y=25 cm and on the front and rear plate-box interfaces are visible.
FIG. 9F is a diagram illustrating the displacement across y-axis for x=25 cm, which compares the results before and after k-space filtering.

FIG. 9A is a screen print of captured data illustrating the recorded time-cross-range displacement for a single transmitter placed at $x_{Tx}=25$ cm (with $x_{Tx}$ being the position of the transmitter). In Arrangement II 412, the excitation corresponds to a cylindrical wave, as opposed to Arrangement I 410, which was a plane wave.

FIG. 9B is a screen print of captured data illustrating the k-space response showing plane wave components propagating in all the possible travelling directions (e.g., filling the k-space domain), as expected for a cylindrical wave.

FIG. 9C is a screen print of captured data illustrating backpropagated displacement on neither the footprint of the box nor the plate edge at y=25 cm, but the wavefront of the cylindrical wave.

FIG. 9D is a screen print of captured data illustrating a filtered k-space d-domain, where only components with $k_x \ll k_y$ remain. To remove non-desired cylindrical wave components, k-space filtering can be applied with small $\alpha$-angle (e.g. $\alpha=5°$). That is, the plane waves travelling along the y-axis are considered.

FIG. 9E is a diagram illustrating backpropagated displacement of the filtered wavemodes, where the reflections happening at y=25 cm and on the front and rear plate-box interfaces are visible. However, for an $\alpha$ angle close to 0°, only the backpropagated displacement across $x=x_{Tx}=25$ cm is recovered, which results in a loss of cross-range resolution. This response is replicated throughout the entire cross-range (e.g., for every x-axis value, or for x-axis values of a particular granularity).

FIG. 9F is a diagram illustrating the displacement across y-axis for x=25 cm, which compares the results before and after k-space filtering.

Figure 10:
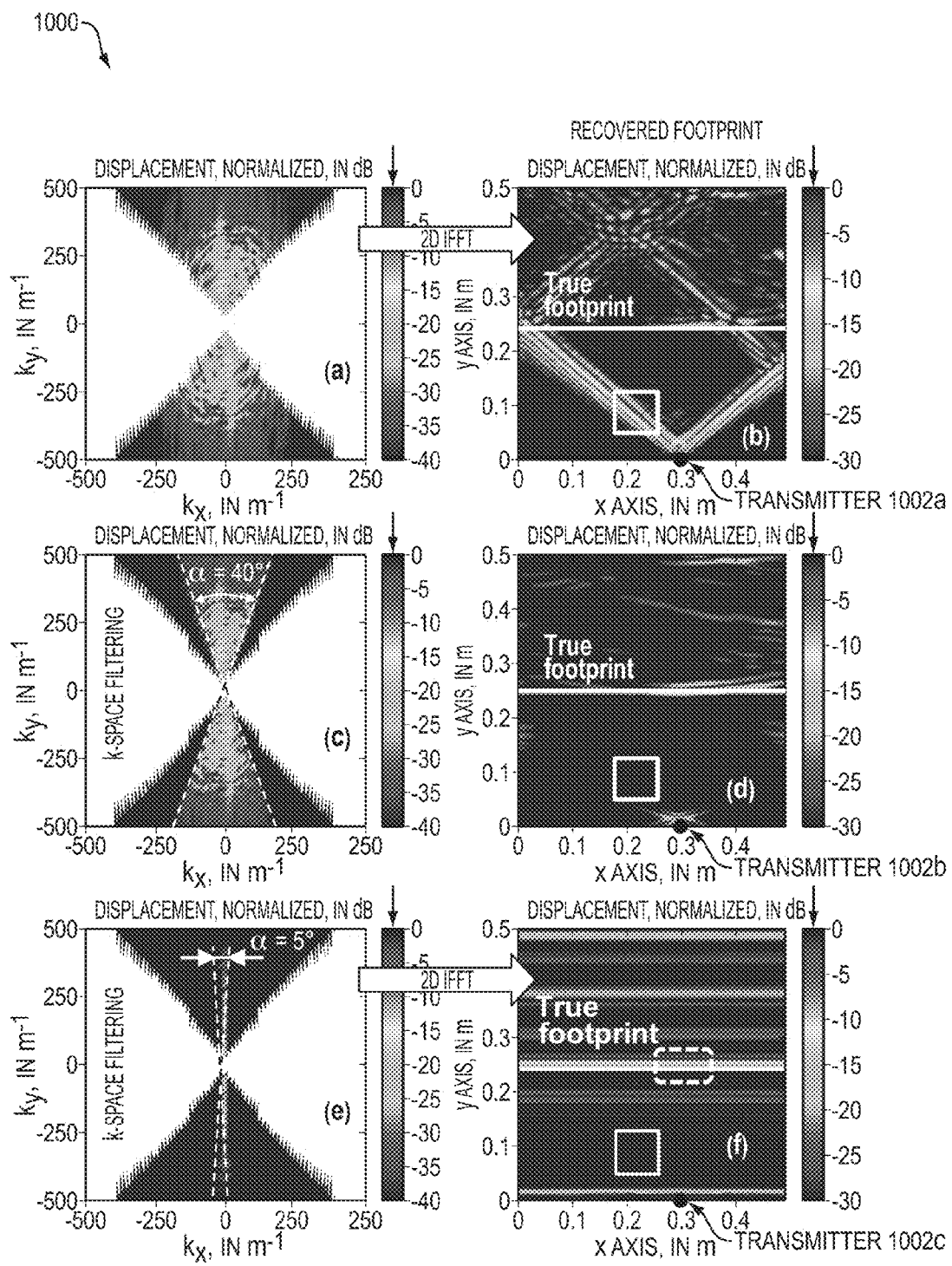
FIG. 10 is a screen print of captured data of k-space filtering, where the filtered displacement in the k-space (i.e., FIGS. 10a, 10c, and 10e, left column plots) and the backpropagated image (i.e., FIGS. 10b, 10d, and 10f, right column plots) is depicted for different α angles.

FIG. 10 is a screen print 1000 of captured data illustrating k-space filtering, where the filtered displacement in the k-space (i.e., FIGS. 10a, 10c, and 10e, left column plots) and the backpropagated image (i.e., FIGS. 10b, 10d, and 10f, right column plots) is depicted for different $\alpha$ angles. In this case, the point source-like transmitter 1002a-c is placed at $x_{Tx}=30$ cm. For $\alpha=40°$, the reflection at y=25 cm and the reflection of the transmitted cylindrical wave on the lateral sides of the metallic plate (located at x=0 and 50 cm, y=15 cm). are noticeable.

Increasing the cross-range imaging resolution can be accomplished by placing more transmitters on the y=0 axis, as depicted in FIG. 4, arrangement II 412. The same k-space filtering as explained before is carried out for the recorded displacement for every transmitter. Moreover, an additional cross-range mask with L=5 cm width, centered on every transmitter, is applied.

Figure 11:
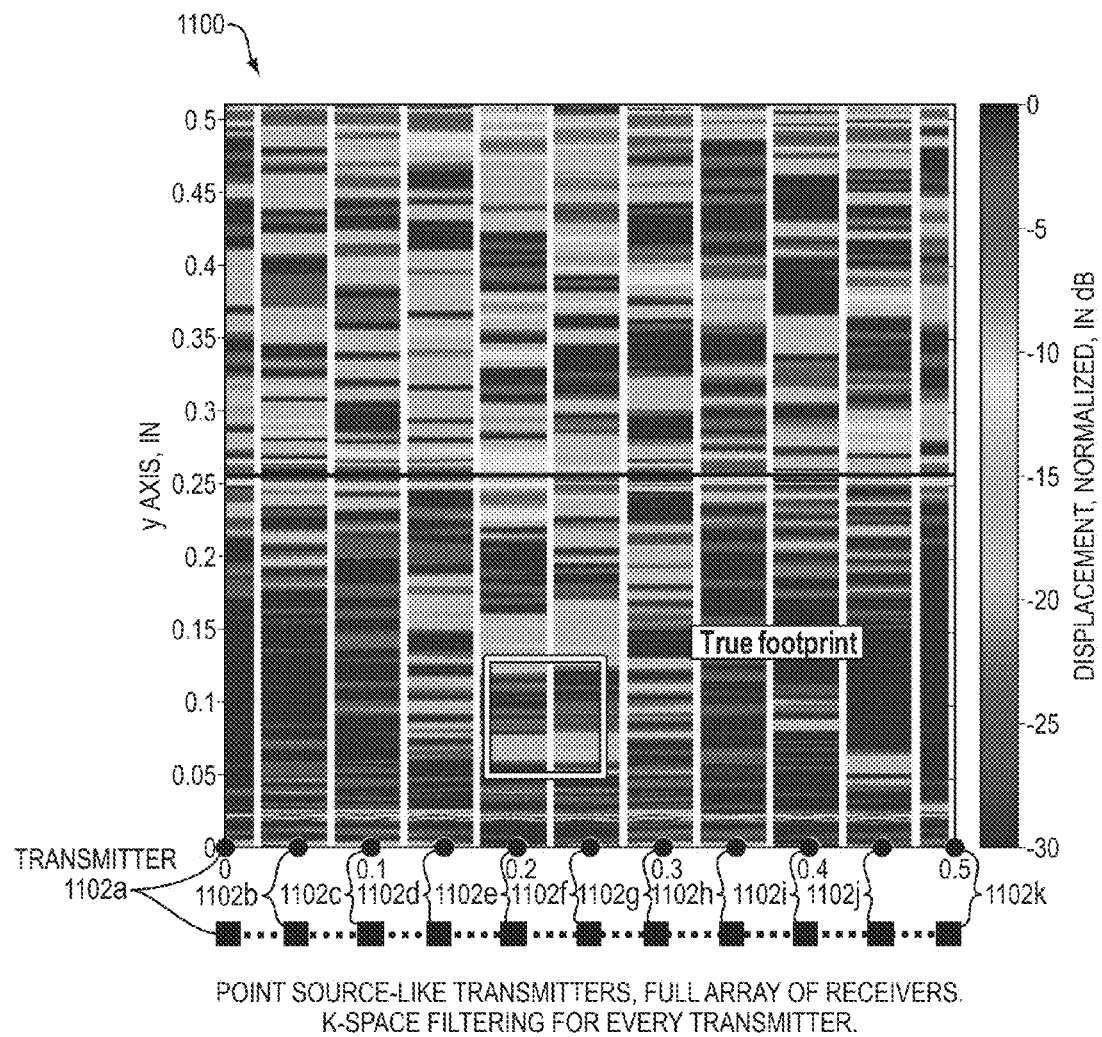
FIG. 11 is a screen print of captured data of imaging results for the considered transmitters.

FIG. 11 is a screen print of captured data illustrating imaging results for the considered transmitters 1102a-k. In this particular embodiment, there are 11 transmitters 1102a-k, but a person of ordinary skill in the art can envision other numbers of transmitters. Note that for every L=5 cm section, the image remains constant across x-direction. Increasing the number of transmitters increases the granularity of the image along the x-direction and leads to the same image as in FIG. 7C.

Practical implementation of the ultrasound imaging system using the transmitting and receiving arrangement II 412 of FIG. 4 supposes an advantage with respect to arrangement I 410 as the number of transmitters is reduced from 50 to 11, although the number of receivers is still high: 50 receivers evenly spaced in the 50 cm length edge are used.

This issue is studied with the transmitting and receiving arrangement presented in arrangement III 414, comprising of a single transmitter and an array of receivers of length $L_{Rx}$. Separation between receiving elements is again 1 cm. The transmitter and the receiving array are displaced in 5 cm-step along the x=0 side of the plate, then applying the same cross-range mask as for imaging results with Arrangement II. In practical, this is equivalent to the configuration of FIG. 1, where the ultrasound sensor is static while the truck moves through the scanning facility.

Figure 12A:
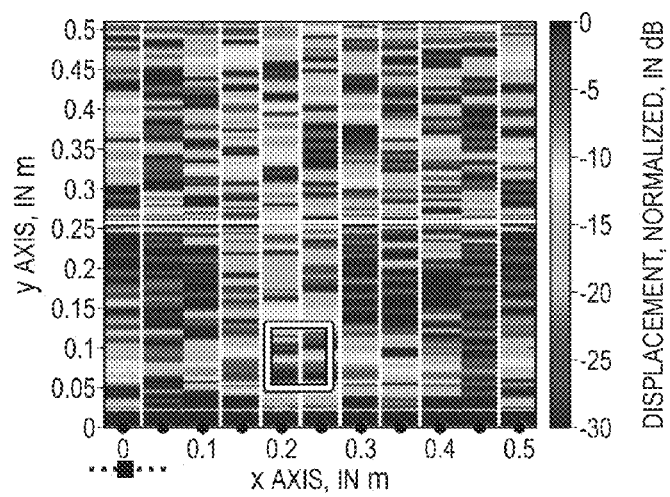
FIGS. 12A-C are screen prints of captured data of arrangement III.
Figure 12B:
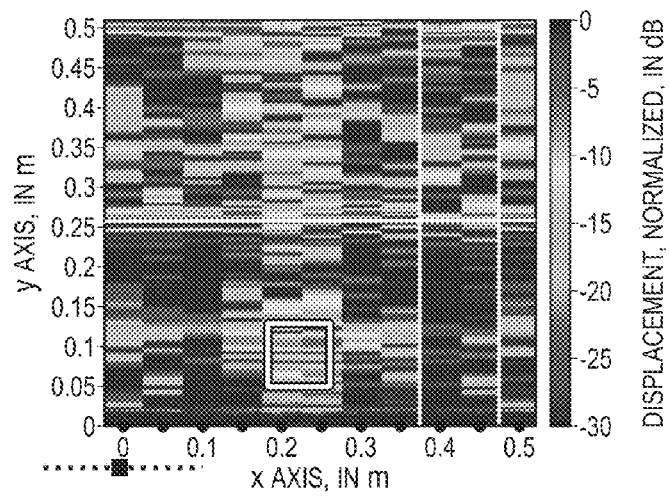
Figure 12C:
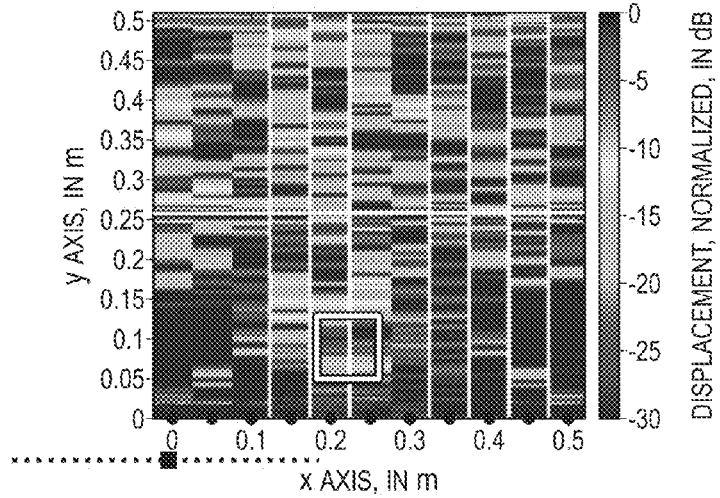

FIGS. 12A-C are screen prints of captured data illustrating arrangement III 414. The parameter to be swept is $L_{Rx}$. FIGS. 12A, 12B, and 12C, show imaging results for $L_{Rx}=10$ cm, 20 cm, and 40 cm, respectively. For every case, the number of receiving elements is 10, 20, and 40. As expected, cross-range resolution is reduced for smaller receiving arrays (FIG. 12A). A $L_{Rx}=40$ cm receiving array yields similar resolution as the full receiving array of arrangement II 412.

Arrangements I, II, and III 410, 412, and 414, respectively, can be analyzed using phased array theory. There are two main kinds of approaches for imaging systems: conventional full phased array (FPA) imaging, which produces the best image quality by using all elements for both transmission and reception, and classical synthetic aperture (CSA) imaging, with one transmitter or receiver element at the same time. FPA requires complex hardware to synchronize transmission and reception, whereas CSA image is created by coherently combining the images for multiple positions, thus simplifying hardware complexity.

Figure 13A:
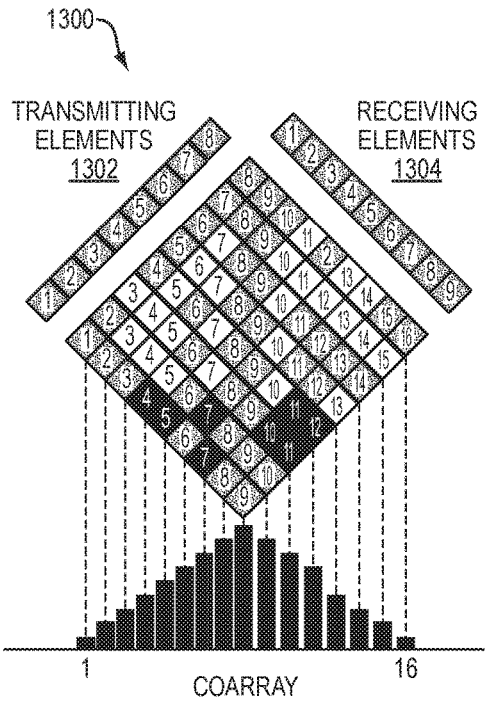
FIGS. 13A-C are diagrams illustrating of comatrix representation, where each transmit/receive element pair contributes to a specific bin of the coarray and the resulting coarray function.
Figure 13B:
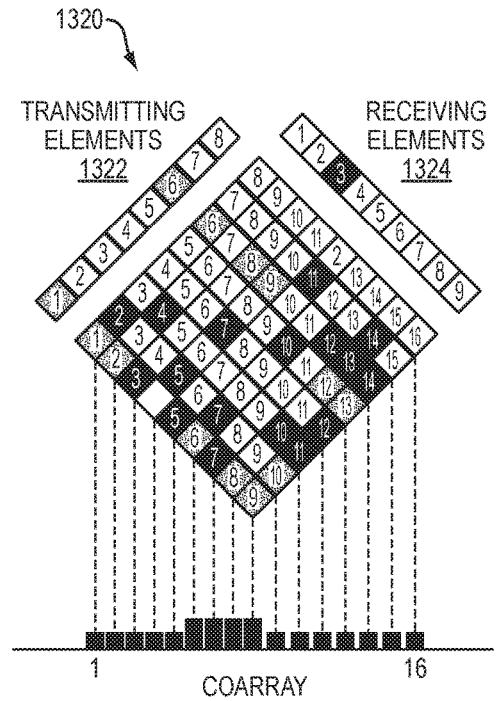
Figure 13C:
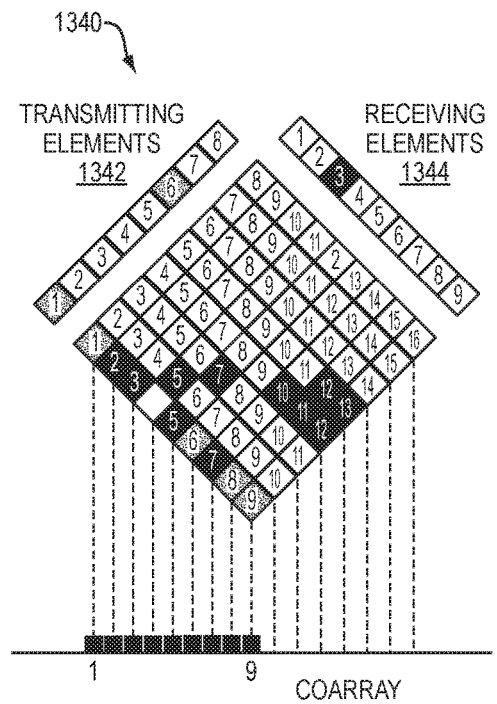

An idea of the effective aperture is given by the convolution of the transmit and receive aperture functions, and is denoted coarray. FIGS. 13A-C are diagrams 1300, 1320 and 1340 illustrating comatrix representation, where each transmit/receive element pair (e.g., 1302 and 1304, 1322 and 1324, and 1342 and 1344) contributes to a specific bin of the coarray and the resulting coarray function. FIGS. 13A, 13B and 13C correspond with arrangements I, II, and III 410, 412 and 414, respectively. For illustration purposes, arrays of 8 elements are considered. Arrangement I, which corresponds to a FPA, produces the highest coarray function, thus resulting in the highest image resolution. If one out of five transmitting elements 1322 are considered (arrangement II), sparse transmitting array), the resulting coarray function is flattened, resulting in loss of resolution, as noticed in FIG. 11. Finally, Arrangement III exhibits a narrower coarray function, reducing even more the resolution. To overcome this issue, Arrangement III setup is moved to create a synthetic aperture, as illustrated in FIG. 12.

Once the effectiveness of the k-space filtering has been validated, the imaging capabilities for the detection of metallic containers on cargo can be employed. For the sake of clarity, the transmitting and receiving Arrangement I (full array of transmitters and receivers) is considered again.

Figure 14A:
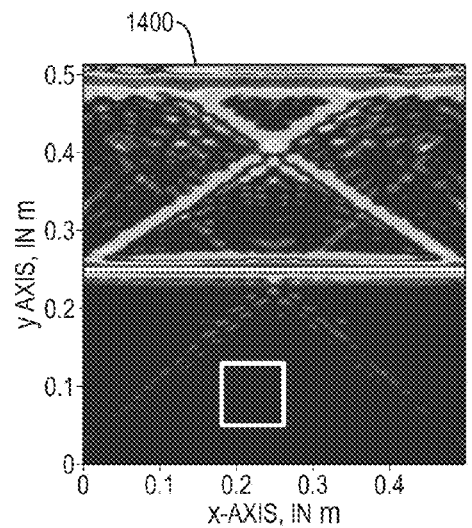
FIGS. 14A-D are screen prints of captured data of the imaging results for four different objects being placed on the metallic surface.
Figure 14B:
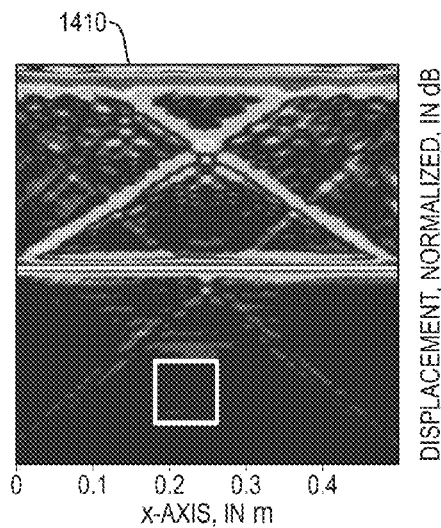
Figure 14C:
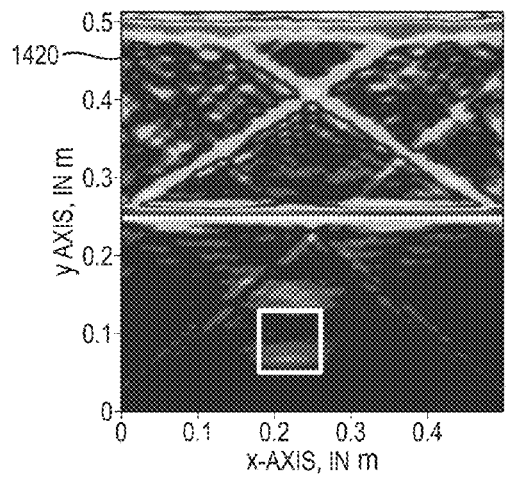
Figure 14D:
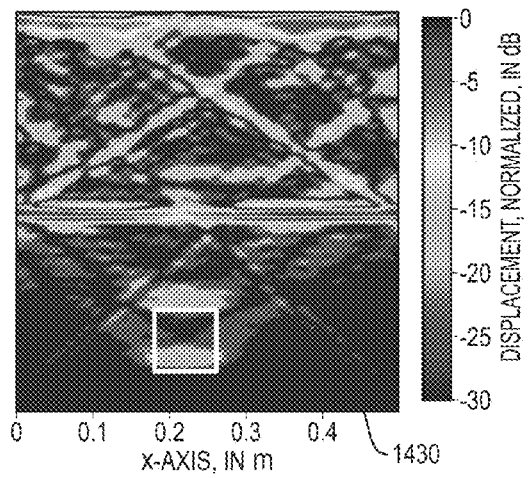

FIGS. 14A-D are screen prints 1400, 1410, 1420 and 1430 of captured data illustrating the imaging results for four different situations: FIG. 14A illustrates a case in which nothing is placed on top of the metallic plate. The only noticeable artifacts are the first and second reflection on the x=25 cm edge, as well as the X-shape waveforms created by edge modes. FIG. 14B is a diagram illustrating shows the footprint when a wooden box (density 1200 kg/m3), having the same dimensions and placed at the same position as the metallic box in FIG. 4, is considered. The reflections in the steel-wood interface are hardly noticeable. FIG. 14C is a diagram illustrating the footprint when a box made of aluminum (density 2700 kg/m$^3$, S-wave velocity 3100 m/s, P-wave velocity 6320 m/s). The aluminum box footprint becomes more noticeable than the wooden box of FIG. 14B. Finally, FIG. 14D is a diagram illustrating to the case with the steel box being on the floor, similar to FIG. 7C.

In connection with FIGS. 14A-D results, aiming to discuss the validity of the proposed method for detecting metallic containers made of high Z-number materials, Table I summarizes the mechanical characteristics and the acoustic impedance of several materials. The aluminum (Z=13) and the lead (Z=82) have very similar acoustic impedance, so they create the same or similar footprint, weaker than steel or iron-made metallic containers, but still detectable.

TABLE I

Mechanical properties and acoustic impedance of several materials.

| Material | Z number | Density (kg/m$^3$) | P-wave velocity (m/s) | S-wave velocity (m/s) | Wave velocity (m/s) | Poisson's ratio | Acoustic impedance (MPa s/m$^3$) |
|---|---|---|---|---|---|---|---|
| Wood | | 1200 | 4200 | 3300 | 2240 | 0.34 | 2.02 |
| Aluminium | 13 | 2700 | 6320 | 3100 | 5100 | 0.35 | 13.77 |
| Iron | 26 | 7870 | 5960 | 3220 | 5200 | 0.29 | 40.92 |
| Steel | | 8000 | 5960 | 3220 | 5000 | 0.29 | 40.00 |
| Copper | 29 | 8960 | 5000 | 2400 | 3750 | 0.34 | 33.60 |
| Gold | 79 | 19700 | 3240 | 1200 | 2030 | 0.40 | 39.99 |
| Lead | 82 | 11400 | 1960 | 700 | 1210 | 0.44 | 13.79 |

FIG. 15 is a diagram 1500 illustrating a container 1502 storing an object 1504 within on an excitation and sensing edge 1506. Containers made of materials with similar characteristics as the guided medium (in this case, a metallic steel plate), can be detected, which is of special interest in case where metallic containers can be concealed somehow within the truck structure, aiming to make them difficult to be detected under a visual inspection. The complexity of the geometry is increased in the example of FIG. 15 by considering a closed metallic container with 1 cm thick walls. This kind of structure requires high energy radiation (e.g., X-ray) to be capable of penetrating the metallic walls for Non Destructive Testing (NDT). Thus, the interest of this example is to efficiently prove the capability of ultrasound imaging to detect a metallic object on the floor of a scaled metallic cargo container. For the sake of clarity, the transmitting and receiving Arrangement I 410 of FIG. 4 is considered.

Figure 16:
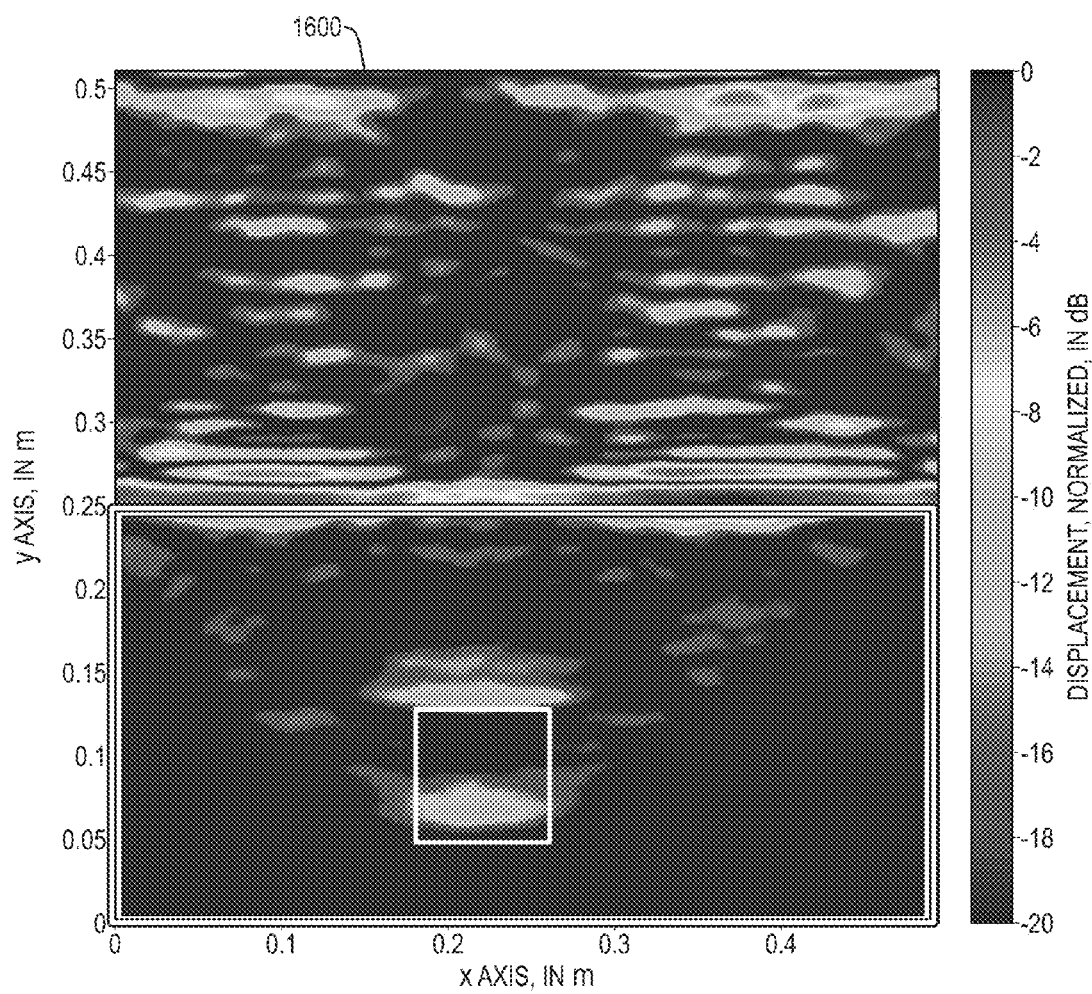
FIG. 16 is a screen print of captured data of a plot of imaging results. Clearly, the reflection at the back side of the metallic container (at x=25 cm) and the reflections on the metallic box—container floor front and rear interfaces being noticeable.

FIG. 16 is a screen print 1600 of captured data illustrating a plot of imaging results. Clearly, the reflection at the back side of the metallic container (at x=25 cm) and the reflections on the metallic box—container floor front and rear interfaces are again noticeable.

FIG. 17 is a diagram 1700 illustrating another example of a container 1702 having objects stored therein on an excitation and sensing edge 1714. The example of FIG. 17 resemble an even more realistic scenario by considering the same or similar closed metallic container 1702 as in the example of FIG. 15, but now storing objects within of different size, shape, and composition. The goal is to show that only the footprint of metallic objects is detected. The container 1702 includes a plastic container containing water 1704, a wooden container 1712, and metallic containers 1707, 1708 and 1710.

Figure 18:
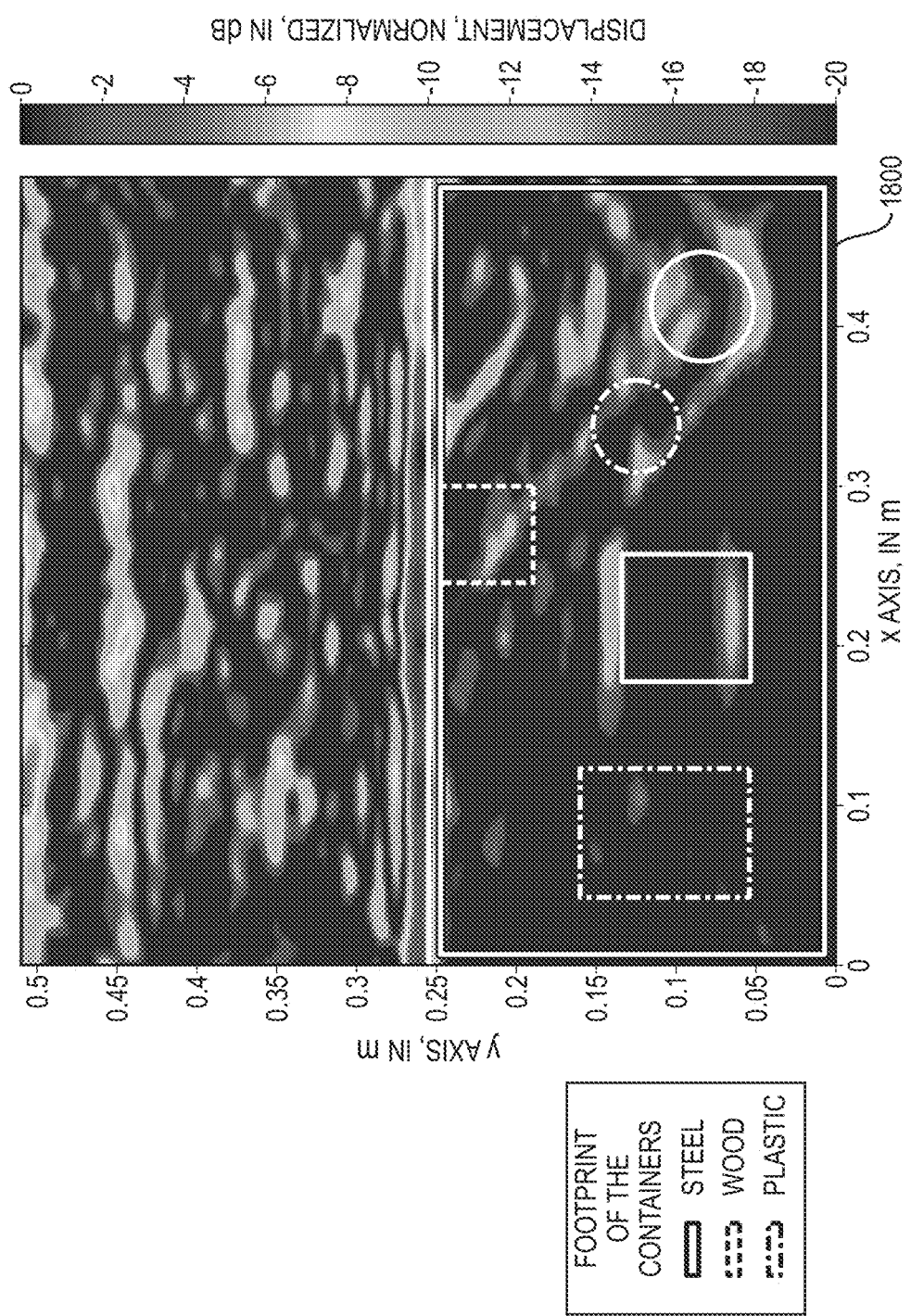
FIG. 18 is a screen view of a representation of the imaged footprint corresponding to the example of FIG. 17.

FIG. 18 is a screen view 1800 of a representation of the imaged footprint corresponding to the example of FIG. 17. Only steel-made assets footprint is recovered. Note that in the case of the cylindrical metallic object, the tails are more noticeable than the ones for the cubic metallic container (the one marked with a 'radiation hazard' warning sign in FIG. 17).

Figure 19:
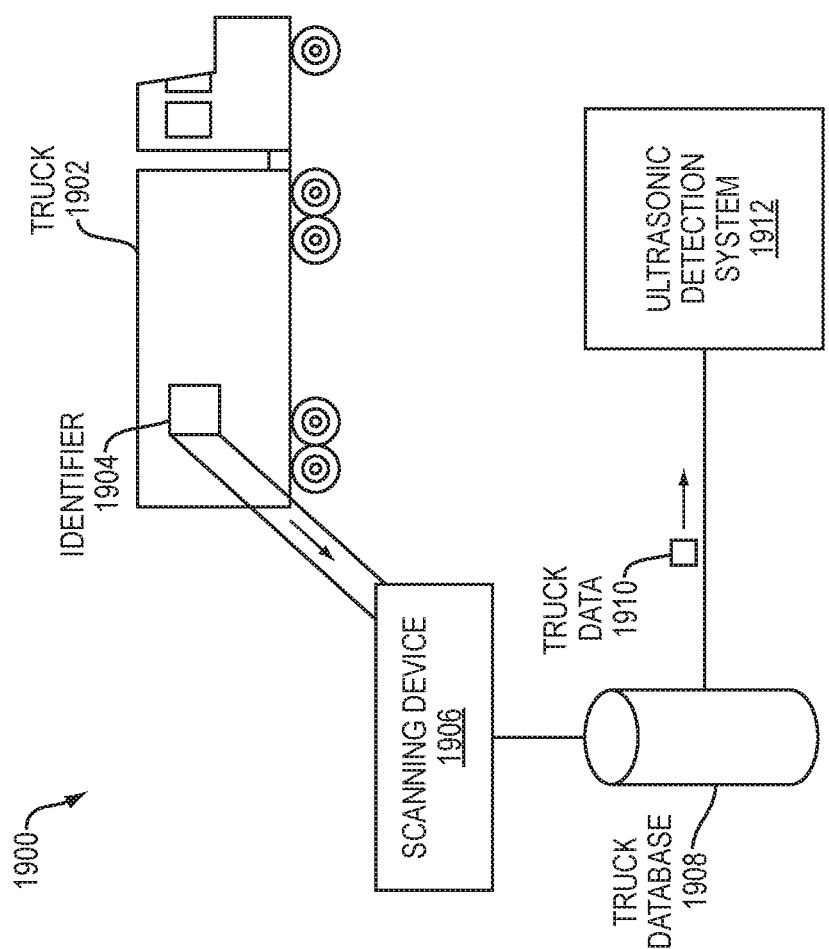
FIG. 19 is a diagram illustrating an example of a truck having an identifier associated therewith.

FIG. 19 is a diagram 1900 illustrating an example of a truck 1902 having an identifier 1904. The identifier 1904 is associated with a truck database 1908 storing each truck's container size, container material type, container material thickness, and any other information about the truck relevant to imaging the surface of the truck using ultrasonic excitations. A scanning device 1906 can read the identifier 1904 of the truck. The identifier 1904 can be a QR code, bar code, alphanumeric string, or license plate number, for example. The scanning device 1906 accesses the truck database 1908, which loads the relevant truck data 1910, as described above, and sends the truck data 1910 to the ultrasonic detection system 1912. The ultrasonic detection system can then automatically configure itself to send ultrasonic excitations configured to the particular truck 1902 based on the truck's properties.

Figure 20:
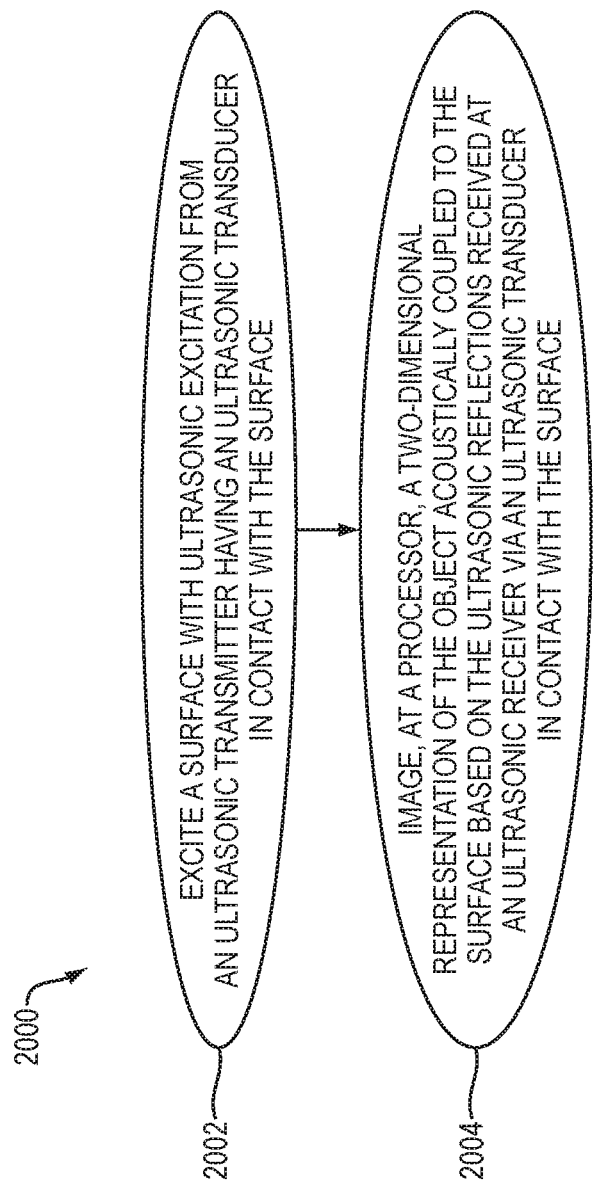
FIG. 20 is a diagram illustrating an example process employed by an embodiment of the present invention.

FIG. 20 is a diagram 2000 illustrating an example process employed by the present invention. The process first excites a surface with ultrasonic excitation from an ultrasonic transmitter having an ultrasonic transducer in contact with the surface (2002). Then, the process images, at a processor, a two-dimensional representation of the object acoustically coupled to the surface based on the ultrasonic reflections received at an ultrasonic receiver in contact with the surface (2004).

Figure 21:
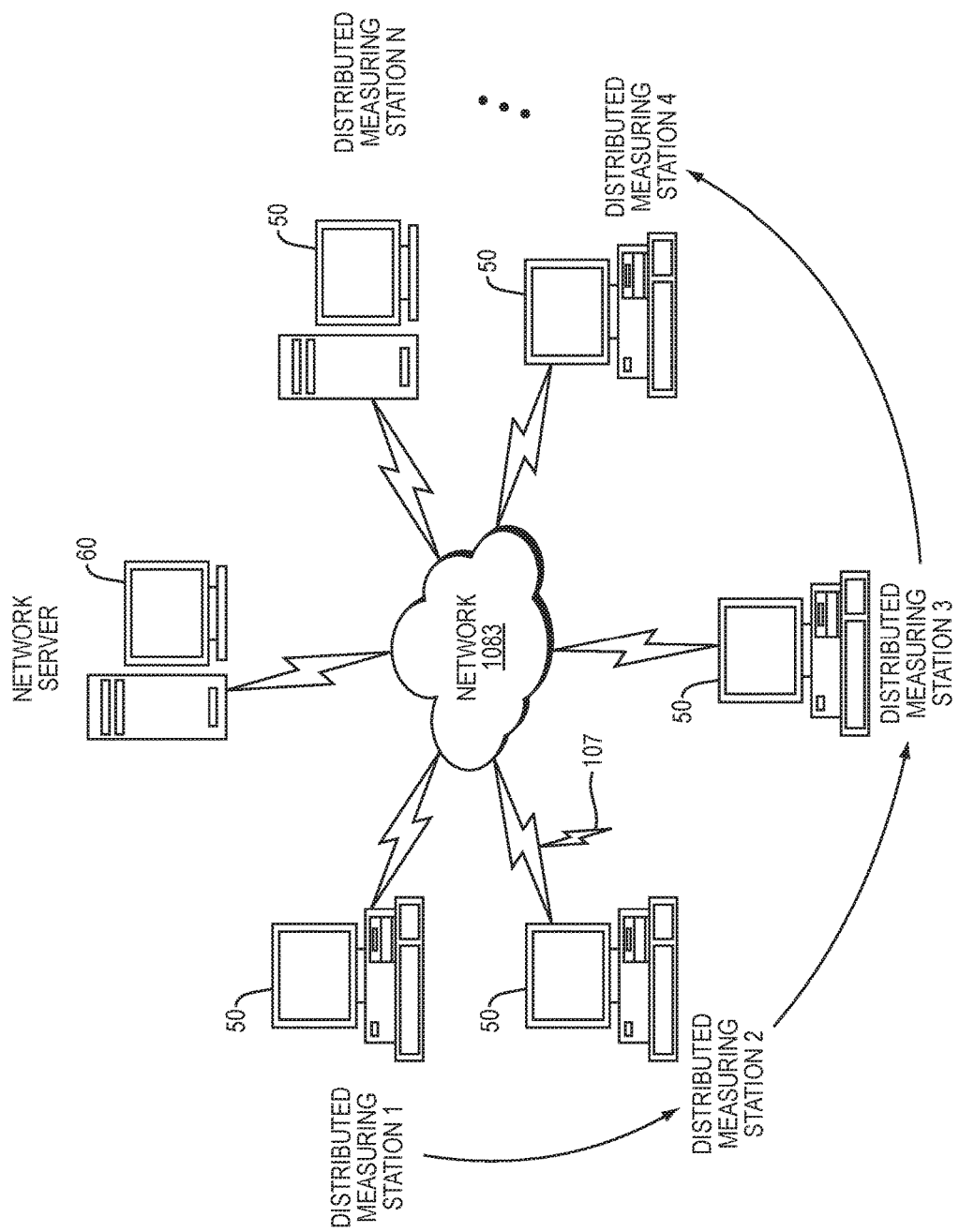
FIG. 21 illustrates a computer network or similar digital processing environment in which embodiments of the present invention may be implemented.

FIG. 21 illustrates a computer network or similar digital processing environment in which embodiments of the present invention may be implemented.

Client computer(s)/devices 50 and server computer(s) 60 provide processing, storage, and input/output devices executing application programs and the like. The client computer(s)/devices/distributed computing stations 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

For example, the client computer(s)/devices 50 can receive excitation data from the transmitter/receiver pairings, for example the ultrasonic units 104 and 114 of FIG. 1. The computer(s)/devices 50 can then send the received data to server computer(s) 60 to perform the image processing to detect the metallic containers on the surface of the truck. Further, the computer(s)/devices 50 can access a database of a server 60 having information the surface dimensions/thickness/material and contents of the truck, which can inform how to send, receive, and process the ultrasonic waves. The computer(s) devices 50 can be configured as distributed measuring stations that emit ultrasonic waves and measure ultrasonic reflections, for processing by the server 60 or other device 50.

Figure 22:
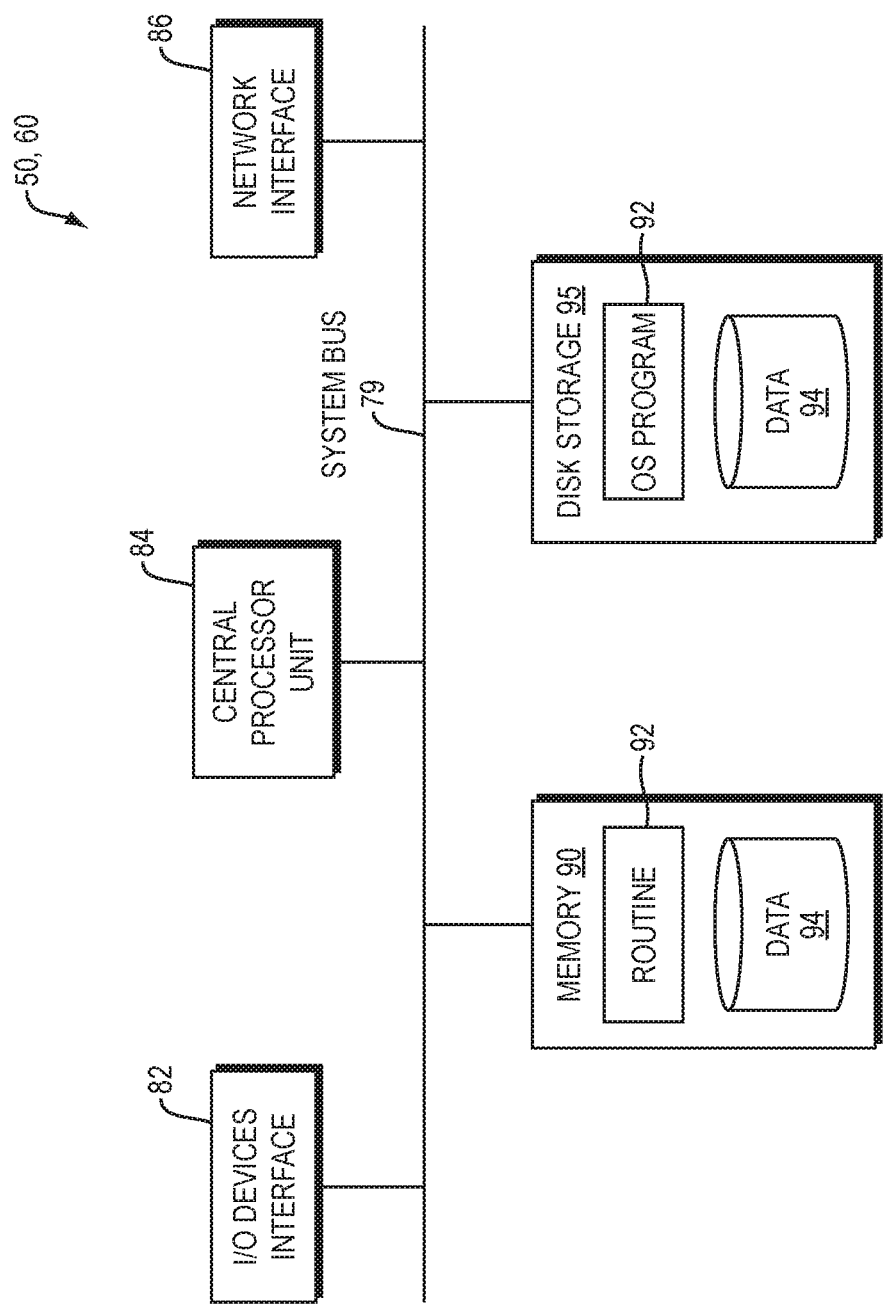
FIG. 22 is a diagram of an example internal structure of a computer (e.g., client processor/device 50 or server computers 60) in the computer system of FIG. 21.

FIG. 22 is a diagram of an example internal structure of a computer (e.g., client processor/device 50 or server computers 60) in the computer system of FIG. 21. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 21). Memory 90 provides volatile storage for computer software instructions 92 and data 94 used to implement an embodiment of the present invention (e.g., imaging code detailed above). Disk storage 95 provides non-volatile storage for computer software instructions 92 and data 94 used to implement an embodiment of the present invention. A central processor unit 84 is also attached to the system bus 79 and provides for the execution of computer instructions.

The disk storage 95, for example, can include information such as surfaces materials/thicknesses/dimensions for each truck, keyed to an identifier, or expected cargo of a truck based on the identifier.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection.

While this invention has been particularly shown and described with references to example embodiments thereof, it will be understood by those skilled in the art that various changes in form and details may be made therein without departing from the scope of the invention encompassed by the appended claims.

What is claimed is:

1. A method for imaging an object on a surface, the method comprising:

exciting a surface with ultrasonic excitation from an ultrasonic transmitter having an ultrasonic transducer in contact with the surface;

moving (i) the surface relative to the ultrasonic transmitter and an ultrasonic receiver or (ii) the ultrasonic transmitter and the ultrasonic receiver relative to the surface; and imaging, at a processor, a two-dimensional representation of the object acoustically coupled to the surface based on ultrasonic reflections received at the ultrasonic receiver in contact with the surface.

2. The method of claim 1, wherein the ultrasonic transmitter is an array of ultrasonic transmitters spanning a substantial length of the surface, and wherein the ultrasonic receiver is an array of ultrasonic receivers spanning the substantial length of the surface.

3. The method of claim 1, further comprising filtering, at the processor, plane waves from the ultrasonic reflections based on (i) time elapsed since exciting the surface and (ii) the size of the surface, the filtering reducing effects of multipath reflections.

4. The method of claim 1, wherein the surface is an internal surface of a container.

5. The method of claim 1, wherein exciting the surface with ultrasonic excitation includes exciting the surface sequentially with a range of frequencies, the range of frequencies based on a thickness of the surface and a material of the surface.

6. The method of claim 5, wherein the surface is associated with an identifier, and further comprising:

based on the identifier, loading representations of a thickness of the surface and a material of the surface; and automatically determining the range of frequencies based on the loaded representations.

7. The method of claim 1, wherein the imaging includes calculating displacement of a wave resulting from the transmitted ultrasonic excitation in the frequency domain by performing a Fourier transform of an observation of the ultrasonic reflections the ultrasonic excitation in the time domain.

8. The method of claim 1, wherein the ultrasonic reflections are received at a plurality of ultrasonic receivers, the plurality of ultrasonic receiver corresponding with the ultrasonic transmitter.

9. The method of claim 1, further comprising exciting the surface by emitting ultrasonic excitations orthogonal to the surface at a point of contact of a transducer of the ultrasonic transmitter.

10. A system for imaging objects on a surface, the system comprising:

an ultrasonic transmitter having an ultrasonic transducer in contact with a surface configured to excite the surface with ultrasonic excitation;

an ultrasonic receiver in contact with the surface configured to receive ultrasonic reflections of the ultrasonic excitation;

a motion module configured to move (i) the surface or the ultrasonic transmitter and the ultrasonic receiver such that the surface moves relative to the ultrasonic transmitter and the ultrasonic receiver or (ii) the ultrasonic transmitter and the ultrasonic receiver such that the ultrasonic transmitter and the ultrasonic receiver move relative to the surface;

a processor; and a memory with computer code instructions stored therein, the memory operatively coupled to said processor such that the computer code instructions configure the processor to implement an imaging module configured to image a two-dimensional representation of the object acoustically coupled to the surface based on the received ultrasonic reflections.

11. The system of claim 10, wherein the ultrasonic transmitter is an array of ultrasonic transmitters spanning a substantial length of the surface, wherein the ultrasonic receiver is an array of ultrasonic receivers spanning the substantial length of the surface.

12. The system of claim 10, further comprising wherein the processor is further configured to filter plane waves from the ultrasonic reflections based on (i) time elapsed since exciting the surface and (ii) the size of the surface, the filtering reducing effects of multipath reflections.

13. The system of claim 10, wherein the surface is an internal surface of a container.

14. The system of claim 10, wherein the ultrasonic transmitter is further configured to excite the surface with ultrasonic excitation by exciting the surface sequentially with a range of frequencies, the range of frequencies being based on a thickness of the surface and a material of the surface.

15. The system of claim 14, wherein the surface is associated with an identifier, and the processor is further configured to:

based on the identifier, load representations of a thickness of the surface and a material of the surface; and automatically determine the range of frequencies based on the loaded representations.

16. The system of claim 10, wherein the processor is further configured to image by calculating displacement of the wave resulting from the transmitted ultrasonic excitation in the frequency domain by performing a Fourier transform of an observation of the ultrasonic reflections of the ultrasonic excitation in the time domain.

17. The system of claim 10, wherein the ultrasonic receiver includes a plurality of ultrasonic receivers corresponding with the ultrasonic transmitter.

18. The system of claim 10, wherein the ultrasonic transmitter is further configured to excite the surface by emitting ultrasonic excitations orthogonal to the surface at a point of contact of a transducer of the ultrasonic transmitter.

* * * * *